US009987312B2

(12) United States Patent
Miyamoto et al.

(10) Patent No.: US 9,987,312 B2
(45) Date of Patent: Jun. 5, 2018

(54) MIXTURE, DISSOLVING SOLUTION AND PHARMACEUTICAL AGENT EACH COMPRISING THERMOPHILIC MICROORGANISM

(71) Applicants: Japan Eco-Science Co., Ltd., Chiba-shi, Chiba (JP); National University Corporation Chiba University, Chiba-shi, Chiba (JP); National University Corporation Kanazawa University, Kanazawa-shi, Ishikawa (JP); Independent Administrative Institution National Fisheries University, Shimonoseki-shi, Yamaguchi (JP); Miroku Co., Ltd., Kitsuki-shi, Oita (JP); Keiyo Plant Engineering Co., Ltd., Ichikawa-Shi, Chiba (JP)

(72) Inventors: Hirokuni Miyamoto, Chiba (JP); Hiroaki Kodama, Matsudo (JP); Takumi Nishiuchi, Kanasawa (JP); Teruo Matsushita, Shimonoseki (JP); Hisashi Miyamoto, Kitsuki (JP); Sankichi Horiuchi, Kashiwa (JP); Manami Seta, Matsudo (JP); Kenichi Mori, Chiba (JP); Masahira Hattori, Kashiwa (JP); Kazuo Ogawa, Ichikawa (JP)

(73) Assignees: JAPAN ECO-SCIENCE CO., LTD., Chiba (JP); NATIONAL UNIVERSITY CORPORATION CHIBA UNIVERSITY, Chiba (JP); NATIONAL UNIVERSITY CORPORATION KANAZAWA UNIVERSITY, Ishikawa (JP); INDEPENDENT ADMINISTRATIVE INSTITUTION NATIONAL FISHERIES UNIVERSITY, Yamaguchi (JP); MIROKU CO., LTD., Oita (JP); KEIYO PLANT ENGINEERING CO., LTD., Chiba (JP)

( * ) Notice: Subject to any disclaimer, the term of this patent is extended or adjusted under 35 U.S.C. 154(b) by 317 days.

(21) Appl. No.: 14/795,868

(22) Filed: Jul. 9, 2015

(65) Prior Publication Data

US 2015/0306153 A1 Oct. 29, 2015

Related U.S. Application Data

(63) Continuation of application No. 13/577,314, filed as application No. PCT/JP2011/052735 on Feb. 9, 2011, now abandoned.

(30) Foreign Application Priority Data

Feb. 10, 2010 (JP) .................................. 2010/028204
Feb. 10, 2010 (JP) .................................. 2010/028205

(51) Int. Cl.
*A61K 35/741* (2015.01)
*C12R 1/01* (2006.01)
*C12R 1/07* (2006.01)

(52) U.S. Cl.
CPC .............. *A61K 35/741* (2013.01); *C12R 1/01* (2013.01); *C12R 1/07* (2013.01)

(58) Field of Classification Search
CPC .............................. A61K 35/741; C12R 1/07
See application file for complete search history.

(56) References Cited

U.S. PATENT DOCUMENTS 6,022,537 A * 2/2000 Combet-Blanc .......... C12R 1/07
424/93.1
2009/0280099 A1* 11/2009 Bachman ............. A61K 9/0043
424/93.45

FOREIGN PATENT DOCUMENTS

JP 2003219864 A 8/2003
JP 2009100728 A 5/2009

OTHER PUBLICATIONS

The International Search Report dated Apr. 5, 2011.
(Continued)

*Primary Examiner* — Sharmila G Landau
*Assistant Examiner* — Sheridan Macauley
(74) *Attorney, Agent, or Firm* — McClure, Qualey & Rodack, LLP

(57) ABSTRACT

To provide a mixture, a dissolving solution and a pharmaceutical agent, which contain a thermophilic microorganism
(Continued)

to make it possible to regulate a mucous membrane immune system gene cluster and metabolism-related gene clusters of the intestines and the liver. Each of them is prepared by fermentation of an organic material containing a thermophilic microorganism at a temperature of 50° C. or more and 90° C. or less. By being administered to the animal, it regulates at least one of a mucous membrane immune system gene cluster, a metabolism-related gene cluster in the intestines, and a metabolism-related gene cluster in the liver of the animal. The microorganism includes at least one species of the genus *Bacillus, Oceanobacillus, Paenibacillus, Anoxybacillus, Lysinibacillus, Methanopyrus, Geogemma, Pyrolobus, Pyrodictium, Hyperthermus, Pyrococcus, Pyrobaculum, Thermococcus, Aeropyrum, Aquifex, Thermotoga, Thermodesulfobacterium, Thermus, Geobacillus,* and *Thermomyces.*

2 Claims, 4 Drawing Sheets

(56) References Cited

OTHER PUBLICATIONS

Niisawa, et al., "Microbial Analysis of a Composted Product of Marine Animal Resources and Isolation of Bacteria Antagonistic to a Plant Pathogen from the Compost," J. Gen. Appl. Microbiol, 2008, vol. 54, No. 3,. pp. 149-158.

Miyamoto, et al., "Konetsukin Hakko Sanbutsu no Keiko Toyo ga Rat no Chonai co Saikin-so to Ketsueki Seibun ni Ataeru Eikyo," Journal of Japanese Biochemical Society, 2008, abstract No. 1P-1278.

Miyamoto, et al., "Miriyo Shigen o Katsuoy shita Kinosei Shokuhin Sozal no Kaihatsu," Fermentation of Organic Resources by Thermophilic Bacteria for Recycling, Bio Ind, May 2010, vol. 27, No. 5, pp. 20-25.

Miyamoto, et al., "Konetsusei *bacillus* species no Keiko Toyo ga Rat Chokan no Idenshi Hatsugen ni Ataeru Eikyo," Journal of Japanese Biochemical Society, Dec. 2010, abstract No. 2P-0984.

Tanaka, et al., "Feed Additives with Thermophile-Fermented Compost Enhance Concentrations of Free Amino Acids in the Muscle of the Flatfish Paralichthys Olivaceus," Jl. Gen. Appl. Microbiol, Feb. 2010, vol. 56, No. 1, pp. 61-65.

* cited by examiner

【Fig. 1】
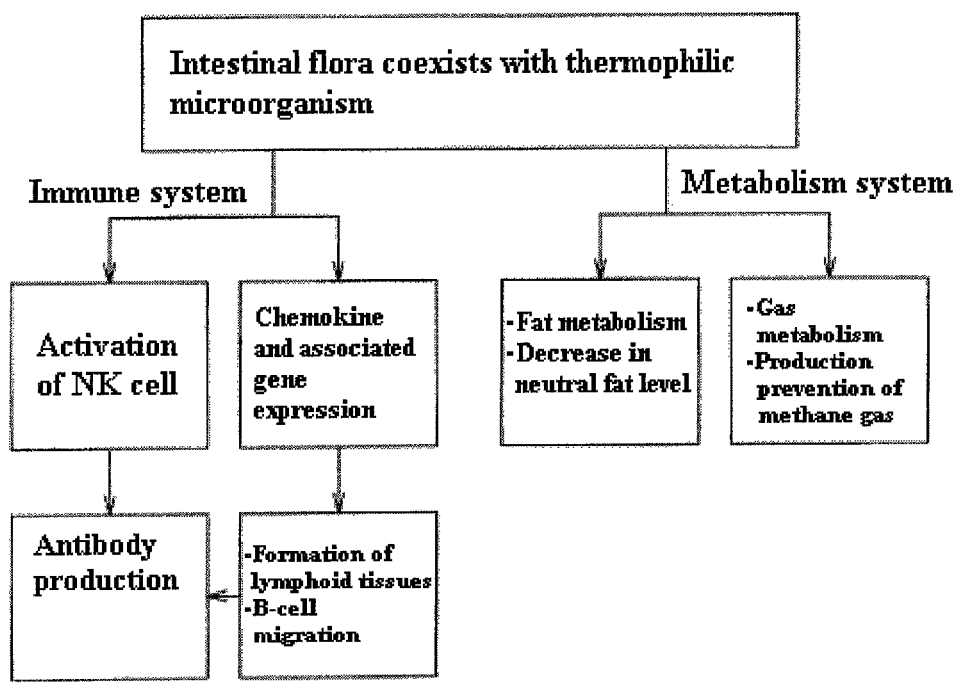

[Fig. 2]
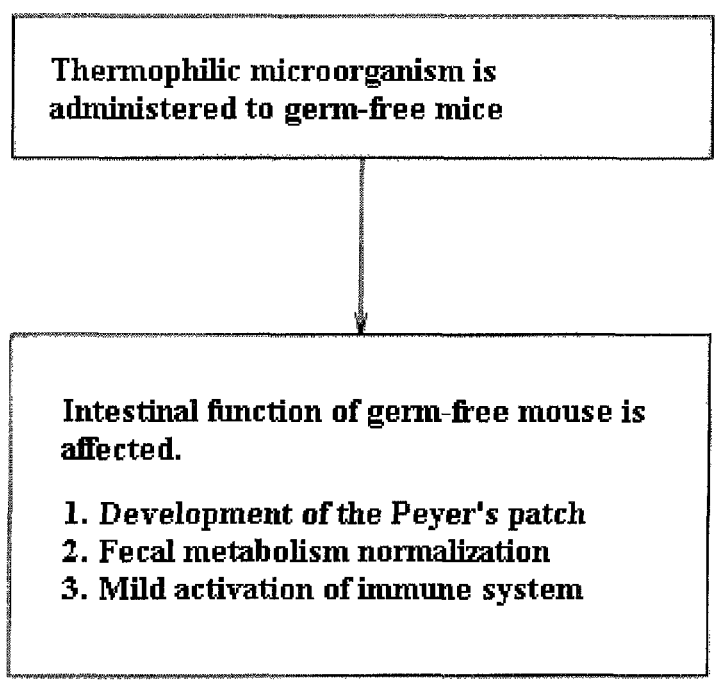
[Fig. 3]
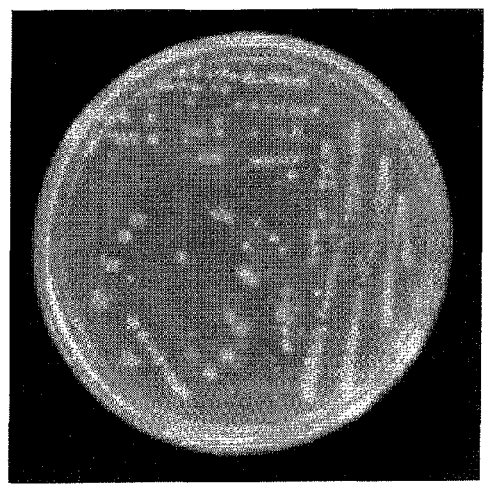

[Fig. 4]
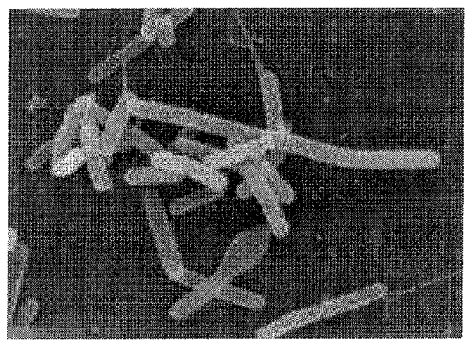
[Fig. 5]
[Fig. 6]
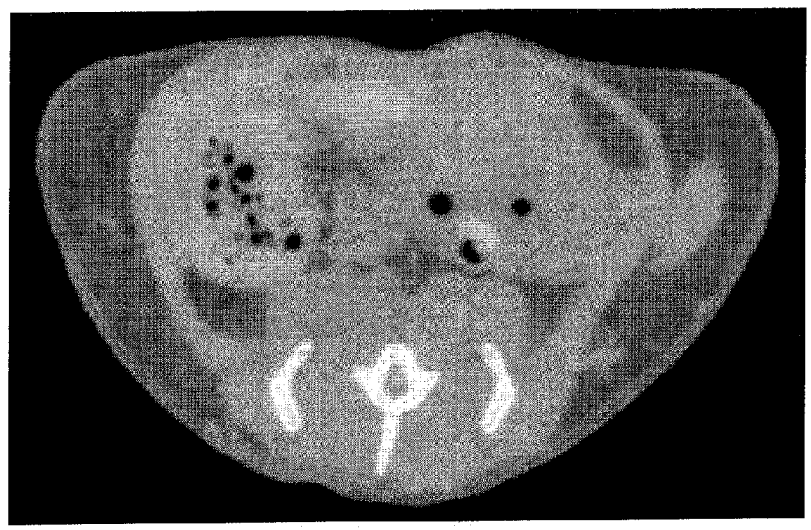

[Fig. 7]
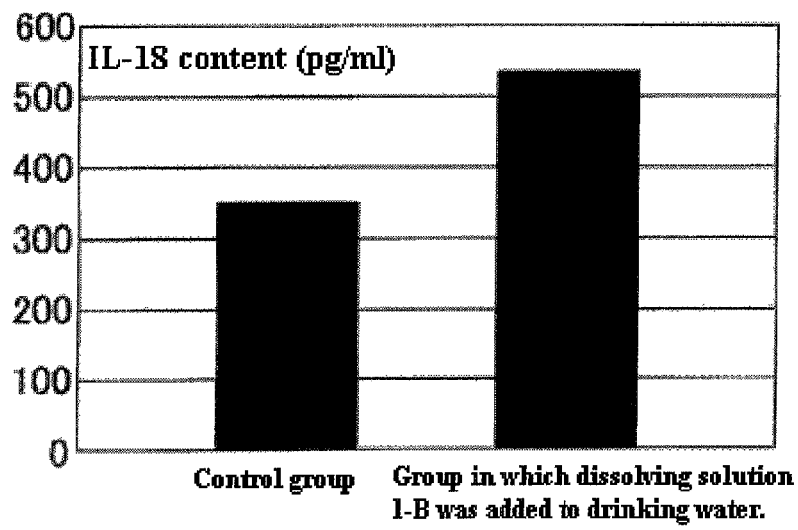
[Fig. 8]
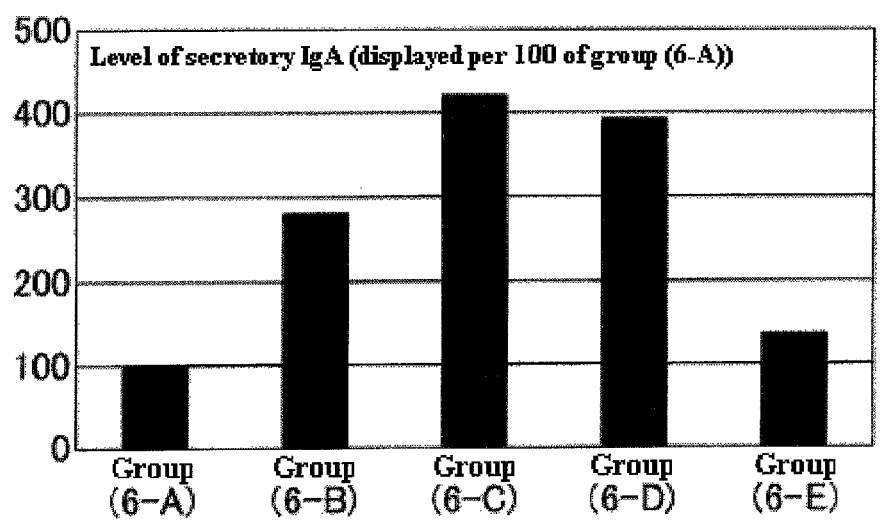

MIXTURE, DISSOLVING SOLUTION AND PHARMACEUTICAL AGENT EACH COMPRISING THERMOPHILIC MICROORGANISM

CROSS-REFERENCE TO RELATED APPLICATION

The present application is a continuation of U.S. application Ser. No. 13/577,314, filed Aug. 6, 2012, which is a U.S. national phase entry of PCT/JP2011/052735, filed Feb. 9, 2011, which claims priority to Japanese application number P2010/028204 filed on Feb. 10, 2010 and Japanese application number P2010/028205 filed on Feb. 10, 2010, the entire contents of which are incorporated herein by reference.

TECHNICAL FIELD

The present invention relates to a mixture, a dissolving solution and a pharmaceutical agent each comprising a thermophilic microorganism, which are capable of activating mucous membrane immune systems and regulating metabolisms of animals including humans.

BACKGROUND ART

Probiotics using microorganisms have been known to improve the enterobacterial flora of animals, prevent diarrhea, activate immunity, and so on. For example, Patent Document 1 discloses pasteurized ingredients derived from bacterial cells to prevent diarrhea in animals. Also, Patent Document 2 discloses a compound containing one kind of lactic acid bacteria, *Lactobacillus*. In addition, Patent Document 3 discloses an antimicrobial compound derived from *Bacillus subtilis*, which is a species of the genus *Bacillus*. Furthermore, Patent Document 4 discloses microorganisms having ability to colonize on the gastrointestinal tract, which are symbionts including Yeast, *Lactobacillus* and *Bifidobacterium*. Furthermore, Patent Document 5 discloses an immunopotentiator including one kind of lactic acid bacteria, such as *Lactobacillus*. Probiotics disclosed in these patent documents are those using microorganisms proliferative at normal temperatures, but not using any thermophilic microorganism.

Furthermore, the followings are examples of influences of administering microorganisms proliferative at normal temperatures to animals on immune systems and metabolic regulations and the action mechanisms of such influences.

In Non-Patent Document 1, it is reported that *Bacillus subtilis* increases CCL21 gene expression by symbiosis with the *Bacteroides* in the appendix of a rabbit. Furthermore, in Non-Patent Document 2, it is reported that *Salmonellas* known as pathogenic bacteria derived from animals inhibit the expression of chemokines CXCL13 and CCL21, which are chemostatic factors for B cells in the immune system, through sensors, Toll-like receptor 4, in the mucous membrane immune system. Furthermore, Non-Patent Document 3 discloses that the above chemokine CXCL13 and the like play a role in development of lymph nodes in the living body, and Non-Patent Document 4 discloses that they relate to the formation of immune functions in the respiratory system.

In Non-Patent Document 5, furthermore, segmented filamentous bacteria are disclosed as bacteria that regulate the functions of the Peyer's patches, the regulatory site of the immune system in the intestinal tract. Furthermore, in Non-Patent Document 6, an attempt to introduce human's flora is also carried out by introduction of the special bacteria such as those described above into germ-free animals (axenic animals).

On the other hand, Patent Documents 6 to 8 disclose techniques using thermophilic microorganisms. The techniques using thermophilic microorganisms have a great advantage in that, for example, they allow organic waste materials to be recycled and thus formulated for respective applications. Each of the above patent documents discloses promotion of making compost from feces and urine, reduction of smells, and the like when administering *Bacillus* having chitin degradation ability to farm animals. However, the mechanisms of action of these techniques are not described in detail. In other words, these patent documents do not disclose direct effects of administration of thermophilic microorganism to an animal on a living body, particularly an influence thereof on the immune or endocrine system.

As described above, any of the conventional techniques for regulating the immune system is just something to use only a microorganism proliferative at normal temperatures. In particular, the conventional techniques cannot simultaneously attain advantageous effects of enhancing muscle-building effects, regulating gas metabolism and fat metabolism to reduce in greenhouse gases generated from intestinal contents, and regulating a fat accumulation in the body. Alternatively, the conventional techniques using thermophilic microorganisms declare effects on manure and feed, and environmental improvement effects.

CITATION LIST

Patent Documents

Patent Document 1: Japanese Patent 2621588
Patent Document 2: Japanese Patent 3338446
Patent Document 3: JP 2006-514019 A
Patent Document 4: JP 2009-137962 A
Patent Document 5: JP 2006-76961 A
Patent Document 6: Japanese Patent 3146305
Patent Document 7: Japanese Patent 3314302
Patent Document 8: JP 2003-219864 A

Non-Patent Documents

Non-Patent Document 1: Nicholas B et al., Microbial induction of B and T cell areas in rabbit appendix. Dev Comp Immunol. 2008; 32(8): 980-981
Non-Patent Document 2: Asheley L st John et al., *Salmonella* disrupts lymph node architecture by TLR-4 mediated suppression of homeostatic chemokines. Nature Medicine 2009; 15(11): 1259-1266
Non-Patent Document 3: Serge A van de Pavert et al., Chemokine CXCL13 is essential for lymph node initiation and is induced by retinoic acid and neuronal stimulation. Nature Immunology 2009; 10(11): 1193-1200
Non-Patent Document 4: Juan E Moyron-Quiroz, et al. Role of inducible bronchus associated lymphoid tissue (iBALT) in respiratory immunity. Nature Medicine. 2004; 10(9): 927-934
Non-Patent Document 5: Klaasen H L B M et al., Infection and Immunity 61: 303-306, 1993 etc.
Non-Patent Document 6: Journal of Intestinal Microbiology 22: 109-114, 2008

SUMMARY OF THE INVENTION

Problems to be Solved by the Invention

However, the techniques disclosed in the respective patent and non-patent documents are insufficient in data for interactive verification between the mechanisms of action about influence on animals and the influence to be affected on general health conditions. In particular, the conventional techniques using thermophilic microorganisms do not relate to the results of researches with experimental animals, and are insufficient in findings about fundamental researches or the like that intend to apply the techniques to animals other than farm animals, specifically to humans.

The present invention has been made in consideration of the above situation, and intends to provide a mixture, a dissolving solution and a pharmaceutical agent using a thermophilic microorganism, which allow regulation of a mucous membrane immune system gene cluster and metabolism-related gene clusters of the intestines and liver based on the data of researches using rats and mice which are experimental animals with accumulated universal data.

Solutions to the Problems

A mixture or a dissolving solution according to the present invention is a mixture or a dissolving solution for regulating at least one of a mucous membrane immune system gene cluster, a metabolism-related gene cluster in the intestines and a metabolism-related gene cluster in the liver of an animal by being administered to the animal, prepared by fermentation of an organic material containing a thermophilic microorganism at a temperature of 50° C. or more and 90° C. or less, wherein the thermophilic microorganism includes at least one species of the genus *Bacillus, Oceanobacillus, Paenibacillus, Anoxybacillus, Lysinibacillus, Methanopyrus, Geogemma, Pyrolobus, Pyrodictium, Hyperthermus, Pyrococcus, Pyrobaculum, Thermococcus, Aeropyrum, Aquifex, Thermotoga, Thermodesulfobacterium, Thermus, Geobacillus, Thermomyces,* and *Clostridium.*

Herein, the above thermophilic microorganism refers to those that meet the criteria for thermostability described in Schlegel, "General Mirobiology" (Thieme Verlag Stuttgart, fifth edition, the column of "173 Highly thermophilic bacteria and extremely thermophilic bacteria") (optimum growth temperature of 40° C. or more).

The mixture or the dissolving solution according to the present invention includes thermophilic mixed bacteria BP-1051 as a thermophilic microorganism.

The mixture or the dissolving solution according to the present invention includes, as a thermophilic microorganism, BP-863 having an ability to degrade persistent sugar, which is a related species of *Bacillus thermoamylovorans.*

The mixture or the dissolving solution according to the present invention includes thermophilic seed bacteria PTA-1733.

The pharmaceutical agent includes either the above mixture or the dissolving solution as an active component.

Effects of the Invention

The mixture or dissolving solution of the present invention includes, as the thermophilic microorganism, at least one of thermophilic microorganisms of the genus *Bacillus, Oceanobacillus, Paenibacillus, Anoxybacillus, Lysinibacillus, Methanopyrus, Geogemma, Pyrolobus, Pyrodictium, Hyperthermus, Pyrococcus, Pyrobaculum, Thermococcus, Aeropyrum, Aquifex, Thermotoga, Thermodesulfobacterium, Thermus, Geobacillus, Thermomyces,* and *Clostridium.* Thus, when administered to animals including humans, the mixture or the dissolving solution is expected to regulate expression of at least one of a mucous membrane immune system gene cluster, a metabolism-related gene cluster in the intestines, a metabolism-related gene cluster in the liver while coexisting with the host intestinal flora. Also, the mixture or the dissolving solution is expected to regulate expression of a mucous membrane immune system gene cluster or the like by administration to animals including humans, under aseptic environment.

The mixture or the dissolving solution of the present invention includes thermophilic mixed bacteria BP-1051 as the thermophilic microorganism. Thus, the natural immune system that promptly responds to bacterial and viral infections can be activated by administration of the mixture or the dissolving solution to animals (including humans) under any of aseptic conditions without the presence of micro flora in the intestines and ordinary environment conditions with the presence of micro flora. Therefore, the mixture or the dissolving solution is expected to regulate expression of a mucous membrane immune system gene cluster, and also regulate expression of gene clusters related to intestine and liver metabolisms.

The mixture or the dissolving solution of the present invention can exert an effect similar to one described above by inclusion of any of BP-863 having an ability to degrade persistent sugar and thermophilic seed bacteria PTA-1773.

In addition, it is assumed that the above BP-863 activates development of the intestinal Peyer's patches and in vitro IL-18 production. Generally the Peyer's patch takes production regulation of immunoglobulin, and IL-18 is known to induce production of gamma interferon. Therefore, the presence of BP-863 contributes to activation of the natural immune system that promptly responds to bacterial and viral infections under aseptic conditions or ordinary environment conditions.

The pharmaceutical agent of the present invention can exert effects similar to those described above by inclusion of either the mixture or the dissolving solution as an active component. In addition, the pharmaceutical agent of the present invention can be administered orally or trans-bronchially to animals including humans.

BRIEF DESCRIPTION OF THE DRAWINGS

FIG. 1 is a conceptual diagram illustrating a work mechanism of a mixture or a dissolving solution of the present invention in the intestinal tract.

FIG. 2 is a conceptual diagram illustrating an influence of the mixture or the dissolving solution of the present invention on the intestinal functions of a germ-free mouse.

FIG. 3 is a photograph of a culture of the related species of *Bacillus thermoamylovorans*, strain N-11 (NITE BP-863).

FIG. 4 is an electron micrographic image of the culture of the related species of *Bacillus thermoamylovorans*, strain N-11 (NITE BP-863).

FIG. 5 is a CT-scan image of the trunk of a mouse fed with high fat food (drinking water: tap water).

FIG. 6 is a CT-scan image of the trunk of a mouse fed with high fat food (drinking water: tap water with dissolving solution 1-B in a concentration of 1.0%).

FIG. 7 is a diagram depicting the content of IL-18 in liver of a germ-free mouse receiving a thermophilic microorganism.

FIG. 8 is a diagram depicting the concentration of secretory IgA in feces of a germ-free mouse receiving a thermophilic microorganism.

EMBODIMENTS OF THE INVENTION

Hereinafter, embodiments of the present invention will be described with reference to drawings. First, a mixture or a dissolving solution of the present invention will be described. The mixture or the dissolving solution of the present invention is obtained by high-temperature fermentation of an organic material containing a thermophilic microorganism. It is administered to animals including humans to regulate expression of at least one of a mucous membrane immune system gene cluster, a metabolism-related gene cluster in the intestines, and a metabolism-related gene cluster in the liver.

The thermophilic microorganism is a microorganism having an optimum growth temperature of 40° C. or more as described in the above description. Specifically, such a microorganism includes thermophilic microorganisms of the genus *Bacillus, Oceanobacillus, Paenibacillus, Anoxybacillus*, and *Lysinibacillus*. The microorganism further includes thermophilic microorganisms of the genus *Methanopyrus, Geogemma, Pyrolobus, Pyrodictium, Hyperthermus, Pyrococcus, Pyrobaculum, Thermococcus, Aeropyrum, Aquifex, Thermotoga, Thermodesulfobacterium, Thermus, Geobacillus, Thermomyces*, and *Clostridium*. More specifically, the microorganism includes thermophilic seed bacteria PTA-1773, thermophilic mixed bacteria BP-1051, the related species (N-11) BP-863 of *Bacillus thermoamylovorans, Bacillus thermocloacae* related species belonging to the genus Firmicutes as a phylum of bacteria (registered under No. AB298562 in GeneBank database), and *Bacillus thermoamylovorans* related species (registered under No. AB298559 in the same database).

In addition, the above thermophilic seed bacteria PTA-1773 are internationally deposited to ATCC (American Type Culture Collection, 10801 University Boulevard Manassas, Va. 20110-2209 U.S.A.) (Accession No: PTA-1773). The thermophilic seed bacteria PTA-1773 include a group of microorganisms with high chitin degradation ability and thermophilic lactic acid bacteria. Specifically, the bacteria PTA-1773 include microorganisms of *Actinomycetales bacterium, Alicyclobacillus, Amphibacillus, Anoxybacillus, Atopostipes, Brachybacterium, Brevibacterium, Cerasibacillus, Clostridium, Corynebacterium, Curtobacterium, Georgenia, Gracilibacillus, Jeotgalicoccus, Salinibacillus, Tissierella, Ureibacillus, Vagococcus, Virgibacillus*, and *Weissella*. Furthermore, thermophilic mixed bacteria BP-1051 are internationally deposited on Jan. 18, 2011 to an independent administrative institution, the Patent Microorganisms Depositary of the National Institute of Technology and Evaluation (NPMD) (2-5-8 Kazusakamatari, Kisarazu-shi, Chiba Prefecture, 292-0818, Japan) (accession No: NITE BP-1051). In addition, *Bacillus thermoamylovorans* related species (N-11), BP-863, is internationally deposited on Jan. 15, 2010 to the independent administrative institution, the Patent Microorganisms Depositary of the National Institute of Technology and Evaluation (NPMD) 2-5-8 Kazusakamatari, Kisarazu-shi, Chiba Prefecture, 292-0818, Japan) (accession No: NITE BP-863).

The organic material includes the thermophilic microorganisms as described above and can be subjected to high-temperature fermentation. Specifically, the organic material includes marine products, farm products, and their residues such as organic wastes and wood chips, which contain the above thermophilic microorganism. Here, the above farm products include raw materials such as corn husk, corn core (corncob), soybean meal, strawberry, and mushroom, which contain persistent sugar alcohols such as arabinose, xylitol, and xylan.

Here, to prepare the mixture or the dissolving of the present invention, the organic material is fermented at a temperature of 50° C. or more and 90° C. or less. Here, if the fermentation temperature of the organic material is lower than 50° C., it is not adequate because the growth of the above thermophilic microorganism may hardly progress and the growth of a microorganism proliferative at normal temperatures may increase. In addition, if the fermentation temperature of the organic material is higher than 90° C., it is not adequate because the thermophilic microorganism may die out.

The mixture or the dissolving solution of the present invention can be prepared from a fermentation product obtained by the above fermentation. For example, the mixture of the present invention can be prepared directly from the fermentation product or from a mixture thereof with feed or the like. Alternatively, the dissolving solution of the present invention can be prepared by dilution of the fermentation product with water. Furthermore, the mixture or the dissolving solution of the present invention can be made by any method with the proviso that the above thermophilic microorganism does not die out.

The mixture or the dissolving solution of the present invention prepared as descried above can be administered to animals (including humans) orally or trans-bronchially to regulate expression of at least one of a mucous membrane immune system gene cluster, a metabolism-related gene cluster in the intestines, and a metabolism-related gene cluster in the liver.

It is assumed that the above functions of the mixture or the dissolving solution of the present invention may result from the mechanism as described, for example, in FIG. 1. In other words, the thermophilic microorganism included in the mixture or the dissolving solution of the present invention acts in the mucous membrane immune system and metabolic system when it coexists with the intestinal flora of the host. Fast, as an action on the mucous membrane immune system, it activates natural killer cells (NK cells) in the intestinal tract and promotes expression of chemokine and the related gene cluster to enhance the formation of lymphoid tissues and migration of B cells, thereby causing an increase in antibody production. Furthermore, as an action on the metabolic system, it regulates the level of expression of gene cluster for fat metabolism to reduce neutral fats or regulates the level of expression of gene cluster for gas metabolism to prevent methane gas production.

Also, it is assumed that the thermophilic microorganism included in the mixture of the present invention or the metabolic system may act on the mucous membrane immune system directly. This is based on the fact that, as illustrated in FIG. 2, in germ free mice (axenic mice) receiving the mixture or the dissolving solution of the present invention, development of the Peyer's patches, normalization of the fecal metabolism, and mild activation of the mucous membrane immune system are performed. Therefore, even if intestinal environment is aseptic, the mixture or the dissolving solution of the present invention may be expressed as probiotics that regulate intestinal metabolism in a manner close to the properties thereof. For example, it is expected to be applied to postoperative therapy requiring nothing by mouth in medical field.

Furthermore, the mixture or the dissolving solution of the present invention can be utilized while being prevented from contamination with various germs because the containing microorganism is thermophilic and sterilization almost at 60° C. is possible before use. Furthermore, the more simple culture technique allows probiotics and pre-probiotics with new functions to be produced in large amount.

Next, the pharmaceutical agent of the present invention will be described. Since the pharmaceutical agent of the present invention includes the mixture or the dissolving solution of the present invention as an active component, it exerts an effect by regulating at least one of a mucous membrane immune system gene cluster, a metabolism-related gene cluster in the intestines and a metabolism-related gene cluster in the liver of an animal receiving the mixture or the dissolving solution of the present. In addition, the present pharmaceutical agent can be administered orally or trans-bronchially to animals (including humans).

If desired, the pharmaceutical agent of the invention can be realized by being mixed with a pharmaceutically acceptable carrier or additive suitably selected from excipients, extending agents, binders, wetting agents, disintegrants, surfactants, lubricants, dispersants, buffers, preservatives, solubilizers, flavoring agents; soothing agents and stabilizers, and formulated in solution, capsule, tablet, granule, or the like.

For example, the excipients include sugars such as milk sugar and saccharide, and starch. The disintegrants include cellulose derivatives and starch. The binders include macromolecules such as gelatin and Arabian gum. The lubricants include waxes and stearic acid.

Hereinafter, the present invention will be described in more detail with reference to examples. However, these examples do not limit the present invention at all. In addition, the contents of the description in each document cited in the examples shall be incorporated herein by reference.

Example 1

(1-1) Preparation of Dissolving Solutions 1-A and 1-B

A dissolving solution 1-A was prepared using a high-temperature fermentation product reported by Niisawa et al. (Niisawa C, Oka S, Kodama H, Hirai M, Kumagai Y, Mori K, Matsumoto J, Miyamoto H, Miyamoto H (2008) Microbial analysis of composted product of marine animal resources and isolation of antagonistic bacteria to plant pathogen from the compost. J Gen Appl Microbiol 54: 149-158) such that the product was diluted 200 times by weight and then subjected to aeration by diffused air at 60 to 70° C. for 6 hours or more. Furthermore, a dissolving solution 1-B was prepared by co-cultivating thermophilic microorganisms included in the dissolving solution 1-A with PTA-1773.

(1-2) Analysis of Microorganisms in Dissolving Solution 1-A

The dissolving solution 1-A includes various kinds of thermophilic microorganisms, and thermophilic mixed bacteria BP-1051 as the dominant bacterial species. Their base sequences (16SrDNA sequences) were analyzed. The analysis was performed such that the microorganisms included in the dissolving solution 1-A were inoculated into standard culture media, nutrient agar culture media, heart infusion culture medium, or the like, and DNAs were then extracted from growing bacterial strains. Furthermore, this analysis employed a known method (Lane, D. J. (1991) 16S/23S rRNA sequencing. In Nucleic Acid Techniques in Bacterial Systematics. Stackebrandt, E. and Goodfellow, M. eds., John Wiley & Sons Ltd., Chichester, England, pp. 115-175) to conduct PCR reaction in which 27F and 1525R were used as universal primers. A reaction solution was prepared by mixing 25 µL of 2× GoTaq Hot Start Colorless Master Mix (Promega Co., WI, USA) and 2 pmole of the primer, and dissolving a sample with 50 µL of sterilized water. A PCR reaction was performed by 94° C. for 15 minutes and then 35 cycles of 94° C. for 30 seconds, 55° C. for 30 seconds and 72° C. for 90 seconds, followed by a reaction at 72° C. for 7 minutes. Furthermore, A PCR fragment of 1.5 kbp in length was purified using QIAquick PCR Purification Kit (Qiagen GmbH, Germany) and the base sequence thereof was then determined by a full-automatic DNA analyzer system (Applied Biosystems Inc., CA, USA) using BigDye Terminator Cycle Sequencing Kit. Furthermore, matching retrieval was performed using database of the GenBank (http://ww.ucbi.ulm.nih.gov/) or the like. The base sequences of the respective microorganisms analyzed by this analysis are represented by SEQ ID NOs. 1 to 8.

Here, *Bacillus badius* related species (IP-2) having a base sequence represented by SEQ ID NO. 1 is 97.3% homologous with the type strain (B NBRC15713$^T$) of *Bacillus badius*. The characteristics of *Bacillus badius* related species (IP-2) include Gram positive, 2 µM in width, 2 µm in length, sporulation, no ability for glycolysis of sugars such as glucose and lactose, catalase positive, oxidase positive, and so on. *Bacillus badius* is known to have gens for nitrogen metabolism.

The related species (IP-3) of *Anoxybacillus kamchatkensis* representing a base sequence in SEQ ID NO. 2 is 99.5% homogenous to the type strain (IAM11061$^T$) of *Anoxybacillus kamchatkensis*. Also, the characteristics of the related species (IP-3) of *Anoxybacillus kamchatkensis* include Gram positive, 0.4 µm in width, 3 to 4 µm in length, sporulation, presence of ability for glycolysis of starch and glucose, catalase positive, oxidase positive, reduction of nitrate into nitrite, and so on. It is assumed that *Anoxybacillus kamchatkensis* may have lipase activity, and a high ability to degrade fat.

The related species (IP-9) of *Virgibacillus pantothenticus* representing a base sequence in SEQ ID NO. 3 is 99.5% homologous to the type strain (DSM14988$^T$) of *Virgibacillus pantothenticus*. Also, the characteristics of the related species (IP-9) of *Virgibacillus pantothenticus* include Gram negative, 0.5 µm in width, 5 to 6 µm in length, large sporulation, presence of ability for glycolysis of starch, glucose, and tagatose, catalase positive, oxidase positive, reduction of nitrate to nitrite, and so on. *Virgibacillus pantothenticus* has ectoine which is a salt-resistant component and known as a moisture-retention component.

The related species (IP-14) of *Bacillus fortis* representing a sequence in SEQ ID NO. 4 is 99.7% homologous to the type strain (LMG22079$^T$) of *Bacillus fortis*. Also, the characteristics of the related species (IP-14) of *Bacillus fortis* include Gram positive, 0.5 µm in width, 1 µm in length, sporulation, no ability for glycolysis of starch and glucose, presence of ability to degrade trehalose, catalase positive, oxidase positive, no reduction of nitrate into nitrite, and so on.

The related species (IP-23) of *Lysinibacillus xylanilyticus* representing a sequence in SEQ ID NO. 5 is 95.0% homologous to the type strain (YC6957$^T$) of *Lysinibacillus xylani-*

*lyticus*. Also, the characteristics of the related species (IP-23) of *Lysinibacillus xylanilyticus* include Gram positive, 0.5 μm in width, 3 to 5 μm in length, sporulation, no ability for glycolysis, presence of ability for peptone degradation, catalase positive, oxidase positive, no reduction of nitrate into nitrite, and so on. *Lysinibacillus xylanilyticus* is known to have a degradation characteristic of persistent xylan. However, the related species (IP-23) of *Lysinibacillus xylanilyticus* may be a new bacterial species because it shows no ability for glycolysis of sugars at all but shows high usage of peptone only.

The related species (IP-60) of *Paenibacillus timonensis* representing a base sequence in SEQ ID NO. 6 is 96.9% homologous to the type strain (CIP108005$^T$) of *Paenibacillus timonensis*. Also, the characteristics of the related species (IP-60) of *Paenibacillus timonensis* include Gram positive, 0.5 μm in width, 3 to 5 μm in length, sporulation, presence of ability for glycolysis of starch, xylitol and xylan, catalase negative, oxidase negative, reduction of nitrate into nitrite, and so on. *Paenibacillus timonensis* is unknown to have ability for glycolysis of xylan. However, the related species (IP-60) of *Paenibacillus timonensis* is assumed as a new bacterial species because of its high xylan degradation ability as described above. Besides, its ability to degrade persistent sugar alcohol is as high as that of BP-863.

The related species (IP-75) of *Paenibacillus curdlanolyticus* representing a base sequence in SEQ ID NO. 7 and is 94.6% homologous to the type strain (IFO15724$^T$) of *Paenibacillus curdlanolyticus*. Also, the characteristics of the related species (IP-75) of *Paenibacillus curdlanolyticus* include Gram positive, 0.5 μm in width, 3 to 5 μm in length, sporulation, presence of ability for glycolysis of lactose, catalase negative, oxidase negative, no reduction of nitrate into nitrite, and so on. *Paenibacillus curdlanolyticus* is known to have a degradation characteristic of persistent xylan. Also, the related species (IP-75) of *Paenibacillus curdlanolyticus* is assumed as a new bacterial species because the ability to degrade persistent sugar alcohol is as high as that of BP-863.

Furthermore, the related species (IP-95) of *Bacillus ruris* representing a sequence in SEQ ID NO. 8 is 99.9% homogenous to the type strain (LMG22866$^T$) of *Bacillus ruris*. Also, the characteristics of the related species (IP-95) of *Bacillus ruris* include Gram positive, 1 μm in width, 2 μm in length, sporulation, presence of ability for glycolysis of starch, glucose and tolehalose, catalase positive, oxidase positive, reduction of nitrate into nitrite, and so on.

Example 2

(2-1) Preparation of Dissolving Solution 2

A dissolving solution 2 was prepared by fermenting an organic material containing marine residues with microorganisms included in the dissolving solution 1-B in an air permeable three-staged fermenter installed in Miroku Co., Ltd at 70° C. or more and 90° C. or less, diluting the final fermentation product 100 times with water, and dissolving it therein at 60° C. or less for 10 hours or more under aeration conditions.

(2-2) Analysis of Microorganism Dominant in Cecal Feces of Germ-Free Mouse with Administration of Dissolving Solution 2

A dissolving solution 2 at a concentration of 0.5% was administered to aseptically breeding Balb/c mice (male, 10 weeks of age) for three weeks, and the base sequences (16SrDNA sequences) of microorganisms isolated from cecal feces of the mice were then analyzed. Here, the above Balb/c mice were bred in isolators (manufactured by ICM Co., Ltd.) in a breeding room controlled at a room temperature of 24±1° C. and a humidity of 55±5%, and the feed used was one sterilized by radiation (product name CMF, manufactured by Oriental Yeast Co., Ltd.). Also, the analysis of the base sequences was carried out by the same method as one described in (1-2) of Example 1. The base sequences of the respective microorganisms in the dissolving solution 2 analyzed by this analysis are represented by SEQ ID NOs. 9 and 10.

The related species (N-11) of *Bacillus thermoamylovorans* representing a base sequence in SEQ ID NO. 9 is the above BP-863 and 99.9% homogenous to the type strain (LMG18084$^T$) of *Bacillus thermoamylovorans*. The biochemical properties of the related species (N-11) of this *Bacillus thermoamylovorans* are listed in Table 1, and photographs of the culture of the related species (N-11) of *Bacillus thermoamylovorans* are shown in FIG. 3 and FIG. 4.

TABLE 1

| Characteristics | Related species (N-11) of *Bacillus thermoamylovorans* | Type bacterial strain (LMG 18084$^T$) of *Bacillus thermoamylovorans* |
|---|---|---|
| Colony and microscopy | | |
| Color of colony | Cream | Cream |
| Shape of bacteria | *Bacillus* | *Bacillus* |
| Dimension of bacteria | 0.5 × 2-5 μm | 0.45-0.5 × 3-4 μm |
| Gram stain | + | + |
| Spore stain | + | + |
| Sporular position | End (subterminal) | End (subterminal) |
| Mobility | V | V (variable among the strain) |
| Other biochemical characteristics | | |
| Indole production | − | − |
| IPA production | − | − |
| H2S production | − | − |
| Ureolysis | − | − |
| Nitrate reduction | + | + |
| Catalase | + | + |
| Oxidase | + | + |

TABLE 1-continued

| Characteristics | Related species (N-11) of *Bacillus thermoamylovorans* | Type bacterial strain (LMG 18084$^T$) of *Bacillus thermoamylovorans* |
|---|---|---|
| Acid-producing ability test | | |
| Glucose | + | + |
| Lactose | + | + |
| Maltose | + | + |
| Galactose | + | + |
| Trehalose | + | + |
| Mannose | + | + |
| Sucrose | + | + |
| Fructose | + | + |
| Cellobiose | + | + |
| Ribose | + | + |
| Xylose | + | V (variable among the strain) |
| Rhamnose | + | − |
| D-arabinose | + | − |
| Turanose | + | ND |
| Sodium gluconate | + | − |
| Inositol | + | − |
| Xylitol | + | − |
| Dulcitol | + | − |
| Erythritol | + | − |
| Sorbitol | + | − |
| Mannitol | + | − |
| Lactic acid | + (weak) | ND |
| Xylan | + | ND |

Here, in Table 1, the biochemical properties of the related species (N-11) of *Bacillus thermoamylovorans* are listed in comparison with the type strain (LMG18084$^T$) of *Bacillus thermoamylovorans*. In addition, the biochemical properties of the type strain (LMG18084$^T$) of *Bacillus thermoamylovorans* are based on the contents of the following documents:

Combet-Blanc, Y., Ollivier, B., Streicher, C., Patel, B. K. C., Dwivedi, P. P., Pot, B., Prensier, G., Garcia, J. L. (1995) *Bacillus thermoamylovorans* sp. nov., a moderately thermophilic and amylolytic bacterium. Int. J. Syst. Bacteriol. 45: 9-16; and Coorevits, A., Logan, N., Dinsdale, A., Halket, G., Scheldeman, P. Heynstrickx, M., Schumann, P., VanLandschoot, A., De Vos, P. (2010) *Bacillus thermolactis* sp. nov., isolated from dairy farms, and emended description of *Bacillus thermoamylovorans*. Int. J. Syst. Microbiol. 56: 781-786.

As shown in Table 1, the related species (N-11) of *Bacillus thermoamylovorans* has high ability to degrade persistent sugar alcohols such as arabinose and xylitol, compared with the type strain (LMG18084$^T$) of *Bacillus thermoamylovorans*. Therefore, the related species (N-11) of *Bacillus thermoamylovorans* is expected, when used in fermentation feed or the like, to have effective ability to degrade corn husk, wheat meal, soybean meal, mushroom, vegetable meal, and so on, which contain persistent sugar alcohols or the like and have conventionally little values as feed. In addition, it is also confirmed that the related species (N-11) of *Bacillus thermoamylovorans* has ability to degrade xylan which is one of persistent polysaccharides. Furthermore, as represented in an electron micrograph in FIG. 4, the related species (N-11) of *Bacillus thermoamylovorans* in spore form coexists with *bacillus* under normal culture conditions.

The related species (N-16) of *Bacillus coagulans* representing a base sequence in the above SEQ ID NO. 10 is 99.9% homogenous to the type strain (ATCC7050$^T$) of *Bacillus coagulans*. The characteristics of the related species (N-16) of *Bacillus coagulans* include Gram positive, 0.7 μm in width, 3 to 5 μm in length, sporulation, no ability to degrade starch, presence of ability for glycolysis of glucose, trehalose and tagatose, catalase positive, oxidase negative, no reduction of nitrate to nitrite, and so on.

(2-3) Preparation of Dissolving Solutions 3, 4 and 5

A dissolving solution 3 was prepared as a dissolving solution containing only the related species (N-11) (BP-863) of *Bacillus thermoamylovorans*. A dissolving solution 4 was prepared as a dissolving solution containing only the related species (N-16) (isolated bacteria containing in BP-1051) of *Bacillus coagulans*. A dissolving solution 5 was prepared as a dissolving solution containing only a type bacterial strain (LMG18084$^T$) of *Bacillus thermoamylovorans*.

Example 3

(3-1) Verification Experiment [1] for Dissolving Solution 1-A

An experiment for verifying a regulatory effect of the dissolving solution 1-A on expression of gene cluster by administration of the dissolving solution 1-A to Wistar rats (male, 3 weeks of age) (obtained from Kyudo Co., Ltd.). In this experiment, the following three groups were prepared and compared with one another.

Group (1-A): A normal feeding group (controls)
Group (1-B): A group in which the dissolving solution 1-A was added to drinking water.
Group (1-C): A group in which the dissolving solution 1-A (but sterilized with 0.02 μm) was added to drinking water.

Here, the Wistar rats used in the experiment were preliminarily bred in groups (1-A) to (1-C) for five days. Furthermore, the Wistar rats were divided into five animals per group and each was bred in its own gauge (manufactured by Natsume Seisakusyo Co., Ltd.). Furthermore, the feed used was one sterilized by radiation (product name MF, manufactured by Oriental Yeast Co., Ltd.). Each Wister rat was fed ad libitum within the intake limits of 25 g per day. In addition, drinking water was taken ad libitum using tap water for the group (1-A), tap water with addition of the dissolving solution 1-A for the group (1-B), and tap water with addition of 1.0% of the dissolving solution 1-A sterilized by 0.02 μm filter for the group (1-C).

The Wistar rats of groups (1-A) to (1-C) were bred for three months, respectively. Subsequently, their intestines, livers, spleens, bloods, and so on were collected and quickly frozen with liquid nitrogen, followed by being stored in a refrigerator at −80° C.

A change in expression of gene cluster in each group was analyzed using the collected small intestines. Specifically, RNA extraction was performed on parts of the collected small intestines, except the Peyer's patches. The RNA extraction was performed by adding 1000 d of Isogen (manufactured by Nippon Gene Co., Ltd.) to a tissue of 100 mg or less, crushing the resultant with a mortar while being frozen by liquid nitrogen, and using RNAeasy mini kit (manufactured by Quiagen). Subsequently, the expression level of each gene cluster was digitized by calculation and calibration of each spot fluorescence level using a array scanner (manufactured by Agilent Co., Ltd.) after hybridization of the extracted RNA on a microarray (manufactured by Agilent Co., Ltd.) on which all genes were mounted and washing thereof. The results are listed in Tables 2 and 3.

TABLE 2

| Gene | Gene Symbol | Regulation |
| --- | --- | --- |
| immunoglobulin related gene | XM_213585, LOC500183, RGD1359539, Z93370, XM_345745, X60291, A2m | up |
| vitamin D-binding protein precursor | TC641315 | up |
| chemokine (C-C motif) ligand | Ccl21b, Scya11, Scya28, Sdf1, LOC498335 | up |
| chemokine (C-C, motif) receptor | Cxcr4, Ccr5, Ccr6, Ccr7 | up |
| nuclear receptor coactivator 7 | XM_574285 | up |
| granzyme B/natural killer cell protease precursor | M_224224, RGD1562700_predicte Gzmb, RGD1562700_predicted | up up |

TABLE 3

| Gene | Gene Symbol | Regulation |
| --- | --- | --- |
| HBV pX associated protein 8 large isoform | Hbxap_predicted | down |
| carbonic anhydrase | ENSRNOT00000051309 | down |
| apolipoprotein A-V | Apoa5 | down |
| endothelin | Edn3 | down |
| heat shock protein 4 | Hspa4 | down |

Table 2 shows upper six gene clusters among those in group (1-B) each having an expression level of 2.0 or more times higher than that of group (1-A). Among these gene clusters, immunoglobulin related gene, chemokine (C-C motif) ligand, chemokine (C-C motif) receptor, and granzyme B/natural killer cell protease precursor are mucous membrane immune system gene clusters, and vitamin D-binding protein precursor is a metabolism-related gene cluster. Furthermore, but not listed in the tables, "tumor necrosis factor receptor" provided as a mucous membrane immune system gene cluster in group (1-B) had an expression level of 1.8 times higher than that in group (1-A).

Furthermore, as the above immunoglobulin related gene, anti-idiotype immunoglobulin M light chain, immunoglobulin gamma2a constant region, NGF-binding Ig light chain, Ig gamma-1, chain C region, gamma-2a immunoglobulin heavy chain, and immunoglobulin kappa chain variable region were confirmed. Furthermore, for the above chemokine (C-C motif) ligand, small inducible cytokine B13 precursor (CXCL13) (B lymphocyte chemoattractant) was significantly expressed. The expression levels were quantified in Real time PCR, showing that group (1-B) had an increasing tendency of 3.6 times (n=3) higher than that of group (1-A).

Table 3 shows upper five gene clusters among those in group (1-B) having an expression level of one half or less times compared with that of group (1-A). Among these gene clusters, HBV pX associated protein is responsible for control of virus infection, carbonic anhydrase for gas metabolism, apolipoprotein A-V for fat metabolism, endothelin for blood pressure regulation, heat shock protein 4 for gene expression, protein function regulation, and intracellular signaling, and so on.

Here, group (1-C) is different from group (1-B) in that changes in expression levels of gene clusters were small with respect to those in group (1-A).

(3-2) Verification Experiment [1] for Dissolving Solution 1-B

The dissolving solution 1-B was administered to germ-free mice to carry out an experiment for verifying a regulatory effect of the dissolving solution 1-B on the expression level of gene cluster. In this experiment, the following two groups were prepared and compared with each other.

Group (2-A): A normal feeding group (controls)
Group (2-B): A group in which the dissolving solution 1-B was added to drinking water.

Here, five germ-free mice (obtained from Laboratory of Veterinary Public Health, Graduate School of Agricultural and Life Sciences, The University of Tokyo, and bred in this laboratory at our request) were used for each of groups (2-A) and (1-B), and bred in the same isolator (manufactured by ICM Co., Ltd.) provided for each group. Furthermore, the feed used was one sterilized by radiation (product name CMF, manufactured by Oriental Yeast Co., Ltd.). The mice were allowed to take the feed ad libitum. Furthermore, drinking water for group (2-A) was water sterilized by UV and autoclave. Drinking water for group (2-B) was water sterilized by UV and autoclave, to which 0.5% of the dissolving solution 1-B was added. The mice were allowed to drink the drinking water ad libitum.

The germ-free mice of groups (2-A) and (2-B) were bred for three weeks, respectively. Subsequently, their intestines, livers, spleens, bloods, and so on were collected and quickly frozen with liquid nitrogen, followed by being stored in a refrigerator at −80° C. A change in expression level of gene cluster in each group was analyzed in the same manner as in the example (3-1).

From the results of the analysis, the following facts were found: in the germ-free mice, administration of the dissolving 1-B led to a small change in number of gene clusters similar to the change in the case of Wistar rats represented in Tables 2 and 3, however, immunoglobulin related gene, chemokine (C-C motif) ligand, and tumor necrosis factor receptor, which are similar mucous membrane immune system gene clusters represented in Table 4, are expressed high, and the expression of metabolism-related gene cluster is also regulated. Here, it is assumed that such results may be due to the effect of short-term administration because a time period of administration to the germ-free mice is as short as three weeks.

TABLE 4

| Gene | Mouse Gene Symbol | Regulation |
| --- | --- | --- |
| immunoglobulin related gene | Igsf9, Igsf3, Semas3b | up |
| chemokine (C-C motif) ligand | Ccl25 | up |
| tumor necrosis factor receptor | Tnfrsf1b | up |

(3-3) Verification Experiment [2] for Dissolving Solution 1-A

The liver of Wistar rat collected in the example (3-1) was subjected to an analysis of a change in expression level of gene cluster in each of groups (1-A) and (1-B). This analysis was performed in the same manner as in the example (3-1). The analytical results are listed in Tables 5 and 6.

TABLE 5

| Gene | Gene Symbol | Regulation |
| --- | --- | --- |
| olfactory receptor 1148 (predicted) | Olr1148 | up |
| immunoglobulin related gene | RGD1562855_predicted, IgK | up |
| UDP glycosyltransferase 2 family, polypeptide B | Olr1330 | up |
| TRAF2 binding protein | LOC310877, Ab2-389 | up |
| alcohol dehydrogenase 6 (class V) | Adh6 | up |

TABLE 6

| Gene | Gene Symbol | Regulation |
| --- | --- | --- |
| mesothelin | Msln | down |
| prolactin receptor | RATPRLR; MGC105486 | down |
| Nocturnin (CCR4 protein homolog) | LOC310395 | down |
| hydroxysteroid (17-beta) dehydrogenase 2 | Hsd17b2 | down |
| apelin, AGTRL1 ligand | Apel | down |
| ring finger protein 187 (predicted) | RGD1308636 | down |
| SNF1-like kinase | Sik | down |
| stearoyl-Coenzyme A desaturase | Scd1, Scd2 | down |

Table 5 shows upper five main gene clusters among those in group (1-B) each having an extremely high expression level compared with that of group (1-A). Among these gene clusters, immunoglobulin related gene is of the mucous membrane immune system, and alcohol dehydrogenase 6 (class V) is of the metabolism-related system. Furthermore, olfactory receptor 1148 (predicted), UDP glycosyltransferase 2 family polypeptide B, TRAF2 binding protein are responsible for other physiological reactions. Furthermore, but not listed in the tables, glucokinase and so on, which were genes of the metabolism-related gene cluster, were also expressed highly.

Here, examples of the immunoglobulin related gene include those of Ig kappa chain, Ig germline kappa-chain C-region gene, 3' end, anti-NG F30 antibody light chain mRNA, variable and constant regions, and immunoglobulin alpha heavy chain.

Table 6 shows upper eight gene clusters among those in group (1-B) being expressed in significantly low level in the liver, compared with that of group (1-A). In these gene clusters, hydroxysteroid (17-bata) dehydrogenase 2 influences an increase or decrease in testosterone, and stearoyl-coenzyme A desaturase influences the entire fat metabolism, such as a decrease in triglyceride. Furthermore, apelin increases in the case of chronic liver disease or obesity.

(3-4) Verification Experiment [2] for Dissolving Solution 1-B

The liver of the germ-free mouse collected in the example (3-2) was subjected to an analysis of a change in expression level of gene cluster in each of groups (2-A) and (2-B). This analysis was performed in the same manner as in the example (3-1). The analysis results are listed in Tables 2 and 3.

TABLE 7

| Gene | Mouse Gene Symbol | Regulation |
| --- | --- | --- |
| major facilitator superfamily domain containing 2 | Mfsd2 | up |
| procollagen, type IV, alpha 2 | Col4a2 | up |
| purinergic receptor P2Y, G-protein coupled 2 | P2ry2 | up |
| ERBB receptor feedback inhibitor 1 | Errfi1 | up |
| glypican 1 | Gpc1 | up |

TABLE 8

| Gene | Mouse Gene Symbol | Regulation |
| --- | --- | --- |
| gene model 837, (NCBI), transcript variant 1 (Gm837) | Thsd7a | down |
| phospholipase C, beta 1 | Plcb1 | down |
| mesothelin | Msln | down |
| solute carrier family 17 | Slc17a8 | down |
| disrupted in renal carcinoma 2 | Dirc2 | down |

Table 7 shows upper five main gene clusters among those in group (2-B) each having an extremely high expression level compared with that of group (2-A). Table 8 shows upper five gene clusters among those in group (2-B) being expressed in significantly low level in the liver compared with that of group (2-A). Here, it is assumed that such results may be due to the effect of short-term administration because a time period of administration to the germ-free mice is as short as three weeks. As is evident from Tables 7 and 8, when comparing with the liver of Wistar rat in the example (3-3), the liver of the germ-free mouse coincides therewith in terms of a significantly decrease in expression level of mesothelin, but does not coincide therewith in terms of other gene clusters.

(3-5) Verification Experiment [3] for Dissolving Solution 1-B

An experiment for verifying a regulatory effect of the dissolving solution 1-B on lipid energy metabolism was performed by administration of the dissolving solution 1-B to Wistar rats (male, 3 weeks of age) (obtained from Kyudo Co., Ltd.). In this experiment, the following four groups were prepared and compared with one another.
Group (3-A): A normal feeding group (controls)
Group (3-B): A group in which regular diet was fed and the dissolving solution 1-B was added to drinking water
Group (3-C): A group bred with high-fat diet Group (3-D): A group in which high-fat diet was fed and the dissolving solution 1-B was added to drinking water.

Here, the Wistar rats used in the experiment were preliminarily bred in groups (3-A) to (3-D) for five days. Furthermore, the Wistar rats were divided into five animals per group and each was bred in its own gauge (manufactured by Natsume Seisakusyo Co., Ltd.). Furthermore, the feed used for groups (3-A) and (3-B) was one sterilized by radiation (product name MF, manufactured by Oriental Yeast Co., Ltd.). The feed used for groups (3-C) and (3-D) was one sterilized by radiation (product name MF, manufactured by Oriental Yeast Co., Ltd.) with addition of lard so as to be 20% in content (prepared in KBT Oriental Co., Ltd.). Each Wister rat was fed ad libitum within the intake limits of 25 g per day. For drinking water, groups (3-A) and (3-C) were allowed to take tap water ad libitum, and groups (3-B) and (3-D) were allowed to take tap water with 1.0% addition of the dissolving solution 1-B ad libitum.

Wistar rats of the above groups (3-A) to (3-D) were bred for three months, respectively. Then, each of them was subjected to collection of blood and so on and weighed. Here, the statistical work handling of weight is carried out by an ANOVA (analysis of variance), and the results are listed in Table 9. Here, NS in the table represents that there is no significant difference.

TABLE 9

| Normal diet Drinking days | Mean value Group (3-A) (LF-C) | Standard deviation | Mean value Group (3-B) (LF-T) | Standard deviation | Significant difference (LF-T vs. LF-C) | Significant difference (C vs. HF-C) |
|---|---|---|---|---|---|---|
| Before experiment | 88.6 | 0.5 | 89.4 | 4.9 | NS | NS |
| Three months after experiment | 485.2 | 35.3 | 486.6 | 49.7 | NS | NS |

| High-fat diet Drinking days | Mean value Group (3-C) (HF-C) | Standard deviation | Mean value Group (3-D) (LF-T) | Standard deviation | Significant difference (HF-T vs. HF-C) | Significant difference (LF-T vs. HF-T) |
|---|---|---|---|---|---|---|
| Before experiment | 88.6 | 3.4 | 88.0 | 2.9 | NS | NS |
| Three months after experiment | 456.8 | 35.7 | 516.4 | 31.7 | $p < 0.05$ | NS |

As is evident from Table 9, there was no significant difference between group (3-A) and group (3-B) with respect to the weights of Wistar rats. However, there was a significant difference between group (3-C) and group (3-D), which were fed with regular diet, with respect to the weights of Wistar rats. In other words, the Wister rats of group (3-D), which was a group in which high-fat diet was fed and the dissolving solution 1-B was added to drinking water, increased in weight in comparison with Wister rats of group (3-C), which was a group bred with high-fat diet.

Here, between group (3-C) and group (3-D), a significant difference was not found in the results of blood analysis of the Wistar rats. Furthermore, significant fat deposition was not found in the Wistar rats in group (3-D) in anatomical findings. In addition, a decrease in number of lipid droplets was found in immunohistological staining of the liver.

(3-6) Verification Experiment [4] for Dissolving Solution 1-B

The dissolving solution 1-B was administered to Balb/c mice (male, 3 weeks of age) (obtained from Kyudo Co., Ltd.) to carry out an experiment for verifying a regulatory effect of the dissolving solution 1-B on fat energy metabolism. In this experiment, the following four groups were prepared and compared with one another.

Group (4-A): A normal feeding group (controls)
Group (4-B): A group in which regular diet was fed and the dissolving solution 1-B was added to drinking water
Group (4-C): A group bred with high-fat diet
Group (4-D): A group in which high-fat diet was fed and the dissolving solution 1-B was added to drinking water.

Here, the Balb/c mice were four or six in one group. In the case of four mice, these mice were bred in one gauge (manufactured by Natsume Seisakusho Co., Ltd.). In the case of six mice, these mice were divided and bred in two gauges (manufactured by Natsume Seisakusho Co., Ltd.). Furthermore, the feed used for groups (4-A) and (4-B) was one sterilized by radiation (product name MF, manufactured by Oriental Yeast Co., Ltd.). The feed used for groups (4-C) and (4-D) was one sterilized by radiation (product name MF, manufactured by Oriental Co., Ltd.) with addition of lard so as to be 20% in content (prepared in KBT Oriental Co., Ltd.). The mice were allowed to take the feed ad libitum. For drinking water, groups (4-A) and (4-C) were allowed to take tap water ad libitum, and groups (4-B) and (4-D) were allowed to take tap water with 1.0% addition of the dissolving solution 1-B ad libitum. Furthermore, the Balb/c mice of groups (4-A) to (4-D) were bred for three months, respectively, and then subjected to measurement of percent of body fat by CT scanning and also weighed.

CT-scanning images of the trunks of the respective Balb/c mice in groups (4-C) and (4-D) were shown in FIGS. 5 and 6, respectively. In the bodies of the Balb/c mice, dark and gray portions on the portion near the peripheries of FIGS. 5 and 6 and the upper center portion shown in FIG. 6. Therefore, even though the Balb/c mice in group (4-D) tends to increase in weight compared with the Balb/c mice in group (4-C), each of them has a little body fat. Actually, the percent of body fat was about 20% lower. In addition, a similar tendency is represented in the femoral regions of the Balb/c mice. The tendency suggests that accumulation of body fat may decrease and the muscle may tend to be built.

(3-7) Verification Experiment [5] for Dissolving Solution 1-B

The dissolving solution 1-B was administered to Wistar rats (male, 3 weeks of age) (obtained from Kyudo Co., Ltd.) and then subjected to an experiment for measuring changes in *Clostridium* clusters IV and *Clostridium* subcluster XIVa, which were *Clostridium* as residential flora in the intestines. In this experiment, the following two groups were prepared and compared with each other.

Group (5-A): A normal feeding group (controls)
Group (5-B): A group in which regular diet was fed and the dissolving solution 1-B was added to drinking water Here, the Wistar rats used in the experiment were preliminarily bred in both groups (5-A) and (5-B) for five days. Furthermore, the Wistar rats were divided into five animals per group and each was bred in its own gauge (manufactured by Natsume Seisakusyo Co., Ltd.). Furthermore, the feed used was one sterilized by radiation (product name MF, manufactured by Oriental Yeast Co., Ltd.). Each Wister rat was fed ad libitum within the intake limits of 25 g per day. For drinking water, group (5-A) was allowed to take tap water ad libitum, and group (5-B) was allowed to take tap water with 1.0% addition of the dissolving solution 1-B ad libitum.

The Wistar rats in the above groups (5-A) and (5-B) were bred for three months, respectively. Subsequently, changes in *Clostridium* clusters IV and *Clostridium* subcluster XIVa in their feces were confirmed using a T-RFLP (Terminal Restriction Frament Length Polymorphism Analysis). The results are listed in Table 10.

TABLE 10

|  | Group (5-A) | Group (5-B) |
| --- | --- | --- |
| Clostridium cluster IV | 3.38 | 7.17 |
| Clostridium subcluster XIVa | 9.50 | 14.04 |

Therefore, it was found that both *Clostridium* cluster IV and *Clostridium* subcluster XIVa were increased in group (5-B) in comparison with group (5-A).

(3-8) Findings Obtained from Verification Experiment for Dissolving Solutions 1-A and 1-B The following findings were obtained by examining the results of the respective experiments described in the examples (3-1) to (3-7).

From the experimental results of the examples (3-1) and (3-3), there is a tendency of activation of the immune system and normalization of functions of the intestines by microorganisms included in the dissolving solution 1-A. For example, anti-IgM antibodies are known to contribute to activation of naive B cells instead of antigen (Mora et al. Generation of Gut-Homing Ig A⁻ secreting B cells by intestinal dendritic cells. Science 2006; 314: 1157-1160). Likewise, furthermore, production of anti-NGF antibodies can be presumed. The anti-NGF antibodies are known to suppress an abnormal increase in Parietal cell permeability in the intestines (Barreau, et al. Pathways involved in gut mucosal barrier dysfunction induced in adult rats by maternal deprivation: corticotrophin-releasing factor and nerve growth factor interplay. J Physiol. 2007; 580(1): 347-356).

Next, from the experimental results of the example (3-1), the microorganisms included in the dissolving solution 1-A caused an increase in expression level of vitamin D-binding protein precursor. The vitamin D-binding protein precursor is known to contribute to the activation of macrophages, and suggested to have anti-cancer functions (Kisker et al., Vitamin D binding protein-Macrophage activating factor (DBP-maf) inhibits angiogenesis and tumor growth in mice. Neoplasia 2003; 5(1); 32-40). Furthermore, the expression level of HBV pX associated protein was decreased. However, the HBV pX associated protein (HBV pX gene) is known to promote p53-induced type cell death.

Also, expression level of carbonic anhydrase was decreased. However, it is known that the carbonic anhydrase is included in the metabolism-regulating system and regulates the amount of carbonate ion. Carbonate ions in feces are a source of methane gas generated from the intestinal flora. Thus, it is expected that a decrease in expression level of carbonic anhydrase may lead to a decrease in methane gas production in the intestines. In a separate experiment, this does not contradict a fact that smells may be decreased at the time of fermentation of feces when high-temperature fermentation feed (feed including a fermentation product containing the same microorganisms as those in the dissolving solution 1-A) is administered. In general, animal feces tend to be anaerobically fermented when subjected to composting, so that methyl mercaptan may be generated from methane gas and hydrogen sulfide in the faces. Therefore, if the feces originally contain methane in small amount, the amount of the methyl mercaptan generated may become small. Furthermore, methane gas has 20 times larger warming coefficient than carbon dioxide. Thus, it is significant if methane gas can be regulated from the inside of the intestines.

Furthermore, the expression level of apolipoprotein A-V is decreased. It is known that a decrease in expression level of apolipoprotein A-V may contribute to a reduction in level of neutral fat as a result of a decrease in its expression level. Furthermore, as a result of analyzing the liver or the like collected in the example (3-1), there is a tendency of a decrease in triglyceride in the serum. A decrease in deposition of triglycerides in the liver is also confirmed by immunohistochemical staining.

Furthermore, in group (1-C) subjected to a sterile treatment, it is suggested that the presence of thermophilic microorganisms is important for exerting a regulatory effect of the expression level of gene cluster based on the fact that no change in expression level of gene cluster for group (1-A) is observed in contrast to group (1-B).

Next, from the experimental results of the example (3-3), an increase in expression level of alcohol dehydrogenase 6 (class V) occurs due to the microorganism clusters in the dissolving solution 1-A. The alcohol dehydrogenase 6 (class V) may be expected to have relevance with fat metabolism. Furthermore, there is a decrease in expression level of mesothelin. This mesothelin is a cancer-related gene cluster and a decrease in expression is considered preferable.

Furthermore, the expression level of Nocturnin is decreased. It is known that the decrease in expression level of Nocturnin tends to cause a decrease in fat level. When the liver collected in the example (3-1) is analyzed, the deposition of neutral fat is decreased and the results do not contradict the decrease in expression level of Nocturnin. In addition, there is a decrease in hydroxysteroid (17-beta) dehydrogenase 2. It is expected that the decrease in hydroxysteroid (17-beta) dehydrogenase 2 may influence on the steroid metabolic system.

Next, the experimental results of the examples (3-2) and (3-4) for germ-free mice suggest that the microorganisms included in the dissolving solution 1-B may directly exert an effect. From the experimental results from the examples (3-1) and (3-3) for Wistar rats, regulatory effects on expression of gene cluster for the mucous membrane immune system and gene cluster for the metabolism system may be obtained by corporation with the flora in the host. However, it is speculated that the direct effects may be different at all.

Next, the experimental results of the examples (3-5) and (3-6) show that the microorganisms included in the dissolving solution 1-B may regulate metabolism of lipid energy in the intestines. Actually, a separate experiment also reveals that the composition of organic acid, which is an enteral energy source, can be changed when high-temperature fermentation feed (containing the same microorganisms as those in the dissolving solution 1-B) is administered.

Next, the experimental results for the example (3-7) show that the microorganisms included in the dissolving solution 1-B can cause an increase in *clostridium* clusters IV and XIVa (*Clostridium leptum* and coccoides groups), which are the resident flora, harmless *Clostridium*. Therefore, it was found that the microorganism included in the dissolving solution 1-B can induce a change in enterobacterial flora of animals receiving the dissolving solution 1-B. It is also considered in combination with the experimental results of the examples (3-5) and (3-6), an increase in *Clostridium* stimulates Toll-like receptor 5 (TLR5) so on to regulate the fat metabolism. Thus, as represented by a CT-scan image shown in FIG. 6, any mechanism may be present to prevent visceral fat from being accumulated even under high-fat diet conditions.

The TLR5, a receptor of the intestinal immune system, acts as a receptor for *Closstridium* or the like having flagella and is considered to regulate the metabolic syndrome as well as regulate the natural immune system. Furthermore, it is reported that a mouse with defected TLR-5 gene becomes metabolic syndrome, and when the enterobacterial flora derived from the mouse is orally administered to a germ-free mouse, the germ-free mouse also becomes metabolic syndrome (Matam Vijay-Kumar, et al. Metabolic Syndrome and Altered Gut Microbiota in Mice Lacking Toll-Like Receptor 5. Science 2010; 328: 228-231). This fact means that metabolic syndrome may be caused when the stimulation with *Clostridium* is not applied through TLR5. Thus, the presence of *Clostridium* as residential flora in the intestines will come under question.

It is also reported that the above *Clostridium* induces control of the intestinal immune system, particularly expression of CD4-positive regulatory T cells (Treg cells), where CD4 expresses transcription factor forkhead box P3(Foxp3), to cause less incidence of inflamed enterocolitis or allergic reaction (Koji Atarashi, et al. Induction of Colonic Regulatory T Cells by Indigenous *Clostridium* Species. Journal Science, electronic edition (published on Dec. 24, 2010), Science 2011, 311 337-341). Furthermore, there is the report that these cells are decreased in the patient with human ulcerative colitis. In addition, the above regulatory T cells are considered to carry an important role about the regulation of the autoimmune disease with a kind of T cells controlling the overactivity of the immune system.

Example 4

(4-1) Verification Experiment [6] for Dissolving Solution 1-B

The dissolving solution 1-B was administered to aseptically breeding Balb/c mice and then subjected to an experiment for verifying the development of the Peyer's patches or the like in the intestinal tract. In this experiment, the following two groups were prepared and compared with each other: a normal feeding group; and a group in which the dissolving solution 1-B was added to drinking water.

In addition, five aseptically breeding Balb/c mice (obtained from Laboratory of Veterinary Public Health, Graduate School of Agricultural and Life Sciences, The University of Tokyo, and bred in this laboratory at our request) were used for each of groups, and bred in the same isolator (manufactured by ICM Co., Ltd.) provided for each group. Furthermore, the feed used was one sterilized by radiation (product name CMF, manufactured by Oriental Yeast Co., Ltd.). The mice were allowed to take the feed ad libitum. Furthermore, drinking water for a control group was water sterilized by UV and autoclave. Drinking water for group (1-B) was water sterilized by UV and autoclave, to which 0.5% of the dissolving solution 1-B was added. The mice were allowed to drink the drinking water ad libitum.

The aseptically breeding Balb/c mice in both groups were bred for three weeks, respectively. Then, after the breeding, the aseptically breeding Balb/c mice in both groups were compared with the control group and showed a tendency to normalize feces of the group in which the dissolving solution 1-B was added to drinking water. Also, comparing with the control group, it is confirmed that the Peyer's patches of the intestinal tract of the group in which the dissolving solution 1-B was added to drinking water can be developed. Furthermore, it is confirmed that the group in which the dissolving solution 1-B was added to drinking water may tend to cause about 1.5 times higher level of the secretary IgA in the colon feces. In addition, the intestinal intensity increased more than the control group and the feces were nearly normal.

(4-2) Verification Experiment [7] for Dissolving Solution 1-B

The dissolving solution 1-B was administered to germ-free mice to carry out an experiment for verifying a change in IL-18 content in the liver. In this experiment, the following two groups were prepared and compared with each other: a normal feeding group (controls); and a group in which the dissolving solution 1-B was added to drinking water.

In addition, five germ-free mice (obtained from Laboratory of Veterinary Public Health, Graduate School of Agricultural and Life Sciences, The University of Tokyo, and bred in this laboratory at our request) were used for each of groups, and bred in the same isolator (manufactured by ICM Co., Ltd.) provided for each group. Furthermore, the feed used was one sterilized by radiation (product name CMF, manufactured by Oriental Yeast Co., Ltd.). The mice were allowed to take the feed ad libitum. Furthermore, drinking water for the control group was water sterilized by UV and autoclave. Drinking water for the group in which the dissolving solution 1-B was added to drinking water was water sterilized by UV and autoclave, to which 0.5% of the dissolving solution 1-B was added. The mice were allowed to drink the drinking water ad libitum.

The Germ free mice of both groups were bred for three weeks, respectively. Then, after the feeding, the livers of the germ-free mice of both groups were analyzed. As a result, comparing with the control group, the content of IL-18 in the liver of the group in which the dissolving solution 1-B was added to drinking water was increased as shown in FIG. 7.

(4-3) Verification Experiment for Dissolving Solutions 2, 3, 4, and 5

Dissolving solutions 2, 3, 4, and 5 were added to Balb/c mouse (male, 3 weeks of age) (obtained from Kyudo Co., Ltd.) and then subjected to an experiment for verifying a change in level of secretory IgA in each of the intestines and spleen, respectively. In this experiment, the following five groups were prepared and compared with one another.

Group (6-A): A normal feeding group (controls)
Group (6-B): A group in which the dissolving solution 2 was added to drinking water.

Group (6-C): A group in which the dissolving solution 3 was added to drinking water.

Group (6-D) A group in which the dissolving solution 4 was added to drinking water.

Group (6-E): A group in which the dissolving solution 5 was added to drinking water.

Furthermore, the Balb/c mice were four or six in each group. In the case of four mice, these mice were bred in one gauge (manufactured by Natsume Seisakusho Co., Ltd.). In the case of six mice, these mice were divided and bred in two gauges (manufactured by Natsume Seisakusho Co., Ltd.). Furthermore, the feed used was one sterilized by radiation (product name MF, manufactured by Oriental Yeast Co., Ltd.). The mice were allowed to take the feed ad libitum. Furthermore, drinking water was tap water for group (6-A), tap water with 1.0% addition of the dissolving solution 2 for group (6-B), tap water with 1.0% addition of the dissolving solution 3 for group (6-C), tap water with 1.0% addition of the dissolving solution 4 for group (6-D), and tap water with 1.0% addition of the dissolving solution 5 for group (6-E). The mice were allowed to take the feed ad libitum.

The Balb/c mice of the above groups (6-A) to (6-E) were bred for three months, respectively, and then subjected to a measurement for the level of secretory IgA in the feces to estimate the level of secretory IgA in each of the intestines and the spleen. Small intestinal data is shown in FIG. 8. As a result of the analysis, the groups (6-B), (6-C), and (6-D) respectively receiving the dissolving solution 2, 3, and 4 showed significant increases in level of secretory IgA, compared with the control group, group (6-A). In addition, it was found that the increment of the secretory IgA level of group (6-E) receiving the dissolving solution 5 with respect to group (6-A) was small, compared with groups (6-B), (6-C), and (6-D). Such tendencies were also confirmed in the spleen.

(4-4) Findings Obtained from Verification Experiment for Dissolving Solutions 1-B, 2, 3, 4, and 5

The following findings were obtained by examining the results of the respective experiments described in the examples (4-1) to (4-3).

The experimental results of the examples (4-1) and (4-2) for aseptically breeding Balb/c mice and germ-free mice suggest that the microorganisms included in the dissolving solution 1-B may have a regulatory effect directly on expression of gene cluster of the mucous membrane immune system. This is because, while in general the Peyer's patches are known to induce the production regulation of immunoglobulin and so on and IL-18 is known to induce production of gamma interferon, from the results of the experiment, it is assumed that the microorganism, such as the related strain (N-11) of *Bacillus thermoamylovorans*, included in the dissolving solution 1-B may activate the development of the Peyer's patches in the intestinal tract and the production of IL-18 in the living body.

Next, the experimental results of the example (4-3) for Balb/c mice suggest that the microorganisms included in the dissolving solution 2 coordinate with the established intestinal flora in the host to exert a regulatory effect on expression of gene cluster of the mucous membrane immune system. Then, the expression level of Foxp3 in the large intestinal tissue, which could be expressed in Treg cells, regulatory cells of the immune system, was investigated using real time PCR. As a result, group (6-C), a single BP-863-administration group, has an expression level of about 1.4 times higher than group (6-A), a normal feeding group (control group), and group (6-E), a type-strain administration group. From the results, it is speculated that the administration of thermophilic BP-863 may accumulate treg cells, which are regulatory cells in the immune system, and an immunoregulation mechanism such as allergic prophylaxis may work.

Furthermore, the related species (N-11) (BP-863) of *Bacillus thermoamylovorans* and the related species (N-16) of *Bacillus coagulans*, which are the microorganisms in the dissolving solution 2, are different from the type bacterial species (LMG18084$^T$) of *Bacillus thermoamylovorans* in that, even in the case of administration as isolated bacteria, it can exert a regulatory effect of expression of gene cluster of the mucous membrane immune system as illustrated in FIG. 8. Furthermore, from the results of the verification examinations for (3-5) and (3-6) of Example 3, and so on, the group receiving the related species (N-11) of *Bacillus thermoamylovorans* is provided with an improved feed efficiency and simultaneously gains a weight equal to or more than the weight of the mice bred with high fat diet 10% or higher calories, resulting an improvement in weight-increasing rate. This may be caused by that the related species (N-11) of *Bacillus thermoamylovorans* breaks down persistent sugar in the feed to increase use efficiency.

INDUSTRIAL APPLICABILITY

The mixture, dissolving solution, and pharmaceutical agent of the present invention can be used as those capable of regulating the mucous membrane immune system gene clusters and the metabolism-related gene clusters in the intestines and liver of an animal by being administered to the animal.

The invention claimed is:

1. A method for administering a mixture or a dissolving solution including BP-863, which is a bacterial species related to *Bacillus thermoamylovorans*, having the ability to degrade persistent sugar, the method comprising administering to an animal orally or trans-bronchially the mixture or the dissolving solution to change enterobacterial flora of the animal and also to regulate expression of at least one of a mucous membrane immune system gene cluster, a metabolism-related gene cluster in the intestines and a metabolism-related gene cluster in the liver of the animal, resulting in activation of the mucous membrane immune system and reduction in accumulation of visceral fat.

2. A method for administering a pharmaceutical agent comprising a mixture or a dissolving solution including BP-863, which is a bacterial species related to *Bacillus thermoamylovorans*, having the ability to degrade persistent sugar, the method comprising administering to an animal orally or trans-bronchially the pharmaceutical agent to change enterobacterial flora of the animal and also to regulate expression of at least one of a mucous membrane immune system gene cluster, a metabolism-related gene cluster in the intestines and a metabolism-related gene cluster in the liver of the animal, resulting in activation of the mucous membrane immune system and reduction in accumulation of visceral fat.

* * * * *

SEQUENCE LISTING

<160> NUMBER OF SEQ ID NOS: 10

<210> SEQ ID NO 1
<211> LENGTH: 1475
<212> TYPE: DNA
<213> ORGANISM: Bacillus badius sp. IP-2

<400> SEQUENCE: 1

```
gacgaacgct ggcggcgtgc ctaatacatg caagtcgagc ggacggaagg gagcttgctc      60
ccggaagtca gcggcggacg ggtgagtaac acgtgggtaa cctgcctgta agactgggat     120
aactccggga aaccggggct aataccggat agcttcttcc tccgcatgga ggaagaatga     180
```

```
aaggcggcct ttggctgtca cttacagatg gacccgcggc gcattagcta gttggtgggg      240
taacggctca ccaaggcgac gatgcgtagc cgacctgaga gggtgatcgg ccacactggg      300
actgagacac ggcccagact cctacgtgag gcagcagtag ggaatcttcc gcaatggacg      360
aaagtctgac ggagcaacgc cgcgtgagtg aagaaggttt tcggatcgta aagctctgtt      420 gtcaggggaag aacaagtacc ggagtcactg ccggtacctt gacggtacct gaccagaaag    480
ccacggctaa ctacgtgcca gcagccgcgg taatacgtag gtggcaagcg ttgtccggaa      540
ttattgggcg taaagcgcgc gcaggcggcc ttttaagtct gatgtgaaag cccacggctc      600
aaccgtggag ggtcattgga aactggaagg cttgagtgca gaagaggaga gcggaattcc      660
acgtgtagcg gtgaaatgcg tagagatgtg gaggaacacc agtggcgaag gcggctctct      720
ggtctgtaac tgacgctgag gcgcgaaagc gtggggagcg aacaggatta gataccctgg      780
tagtccacgc cgtaaacgat gagtgctaag tgttgaggg tttccgccct tcagtgctgc       840
agctaacgca ttaagcactc cgcctgggga gtacggccgc aaggctgaaa ctcaaaggaa      900
ttgacggggg cccgcacaag cggtggagca tgtggtttaa ttcgaagcaa cgcgaagaac      960
cttaccaggt cttgacatcc tctgacacct ctggagacag agcgttcccc ttcgggggac     1020
agagtgacag gtggtgcatg gttgtcgtca gctcgtgtcg tgagatgttg ggttaagtcc     1080
cgcaacgagc gcaaccccttg accttagttg ccagcattca gttgggcact ctaaggtgac    1140
tgccggtgac aaaccggagg aaggtgggga tgacgtcaaa tcatcatgcc ccttatgacc     1200
tgggctacac acgtgctaca atggatggta caaaggcag cgaagccgcg aggtgaagcc      1260
aatcccataa aaccattctc agttcggatt gcaggctgca actcgcctgc atgaagccgg     1320
aatcgctagt aatcgcggat cagcatgccg cggtgaatac gttcccgggc cttgtacaca     1380
ccgcccgtca caccacgaga gtttgcaaca cccgaagtcg gtggggtaac ccttacggga    1440
gccagccgcc taaggtgggg cagatgattg gggtg                                1475
```

<210> SEQ ID NO 2
<211> LENGTH: 1476
<212> TYPE: DNA
<213> ORGANISM: Anoxybacillus kamchatkensis sp. IP-3

<400> SEQUENCE: 2

```
cgaacgctgg cggcgtgcct aatacatgca agtcgagcgg acgattcaaa agcttgcttt      60
tggatcgtta gcggcggacg ggtgagtaac acgtgggcaa cctgccctgt agacggggat     120
aacaccgaga atcggtgct aataccggat aacacgaaag accgcatggt ttttcgttga      180
aaggcggcgc aggctgtcgc tacaggatgg gcccgcggcg cattagctag ttggtgaggt     240
aacggctcac caaggcgacg atgcgtagcc gacctgagag ggtgatcggc cacactggga    300
ctgagacacg gcccagactc ctacgggagg cagcagtagg gaatcttccg caatggacga    360
aagtctgacg gagcaacgcc gcgtgagcga agaaggcctt cgggtcgtaa agctctgttg    420
ttagggaaga acaagtaccg cagtcactgg cggtaccttg acggtaccta cgaggaagc     480 cacggctaac tacgtgccag cagccgcggt aatacgtagg tggcaagcgt tgtccggaat    540
tattgggcgt aaagcgcgcg caggcggttc cttaagtctg atgtgaaagc ccacggctca    600
accgtggagg gtcattggaa actgggggac ttgagtgcag aagaggagag cggaattcca    660
cgtgtagcgg tgaaatgcgt agagatgtgg aggaacacca gtggcgaagg cggctctctg    720
gtctgtaact gacgctgagg cgcgaaagcg tggggagcaa acaggattag ataccctggt    780
```

| | |
|---|---|
| agtccacgcc gtaaacgatg agtgctaagt gttagagggt atccacccct tagtgctgta | 840 |
| gctaacgcat taagcactcc gcctggggag tacgctcgca agagtgaaac tcaaaggaat | 900 |
| tgacggggc ccgcacaagc ggtggagcat gtggtttaat tcgaagcaac gcgaagaacc | 960 |
| ttaccaggtc ttgacatccc ctgacaaccc gagagatcgg gcgttccccc ttcgggggga | 1020 |
| cagggtgaca ggtggtgcat ggttgtcgtc agctcgtgtc gtgagatgtt gggttaagtc | 1080 |
| ccgcaacgag cgcaaccctc gaccttagtt gccagcattc agttgggcac tctaaggtga | 1140 |
| ctgccggcta aaagtcggag gaaggtgggg atgacgtcaa atcatcatgc cccttatgac | 1200 |
| ctgggctaca cacgtgctac aatgggcggt acaaagggtc gcgaacccgc gaggggagc | 1260 |
| caatcccaaa aagccgctct cagttcggat tgcaggctgc aactcgcctg catgaagccg | 1320 |
| gaatcgctag taatcgcgga tcagcatgcc gcggtgaata cgttcccggg ccttgtacac | 1380 |
| accgcccgtc acaccacgag agtttgcaac acccgaagtc ggtgaggtaa cccttacggg | 1440 |
| agccagccgc cgaaggtggg gcaaatgatt ggggtg | 1476 |

<210> SEQ ID NO 3
<211> LENGTH: 1487
<212> TYPE: DNA
<213> ORGANISM: Virgibacillus pantothenticus sp. IP-9

<400> SEQUENCE: 3

| | |
|---|---|
| gacgaacgct ggcggcgtgc ctaatacatg caagtcgagc gcgggaagca agcagatctc | 60 |
| cttcgggggt gacgcttgtg gaacgagcgg cggacgggtg agtaacacgt gggcaaccta | 120 |
| cctgtaagac tgggataacc ccgggaaacc ggggctaata ccggatgata catatcgtcg | 180 |
| catgacgaga tgttgaaagg cggcatatgc tgtcacttac agatgggccc gcggcgcatt | 240 |
| agctagttgg tgagataaaa gctcaccaag gcgacgatgc gtagccgacc tgagagggtg | 300 |
| atcggccaca ctgggactga cacggccc agactcctac gggaggcagc agtagggaat | 360 |
| cttccgcaat ggacgaaagt ctgacggagc aacgccgcgt gagtgatgaa ggttttcgga | 420 |
| tcgtaaaact ctgttgttag ggaagaacaa gtgccattcg aataggttgg caccttgacg | 480 |
| gtacctaacc agaaagcccc ggctaactac gtgccagcag ccgcggtaat acgtaggggg | 540 |
| caagcgttgt ccggaattat tgggcgtaaa gcgcgcgcag gcggtccttt aagtctgatg | 600 |
| tgaaagccca cggcttaacc gtggagggc attggaaact gggggacttg agtacagaag | 660 |
| aggagagtgg aattccacgt gtagcggtga aatgcgtaga gatgtggagg aacaccagtg | 720 |
| gcgaaggcga ctctctggtc tgtaactgac gctgaggtgc gaaagcgtgg gtagcgaaca | 780 |
| ggattagata cccctggtagt ccacgccgta acgatgagt gctaggtgtt aggggggtttc | 840 |
| cgccccttag tgctgaagtt aacgcattaa gcactccgcc tggggagtac ggccgcaagg | 900 |
| ctgaaactca aaagaattga cggggacccg cacaagcggt ggagcatgtg gtttaattcg | 960 |
| aagcaacgcg aagaacctta ccaggtcttg acatcctctg acgcccctag agataggag | 1020 |
| ttcccttcgg ggacagagtg acaggtggtg catggttgtc gtcagctcgt gtcgtgagat | 1080 |
| gttgggttaa gtcccgcaac gagcgcaacc cttgatctta gttgccagca tttagttggg | 1140 |
| cactctaagg tgactgccgg tgacaaaccg gaggaaggtg gggatgacgt caaatcatca | 1200 |
| tgccccttat gacctgggct acacacgtgc tacaatggat ggaacaaagg gcagcgaagc | 1260 |
| cgcgaggcca agcaaatccc ataaaaccat tctcagttcg gattgcaggc tgcaactcgc | 1320 |
| ctgcatgaag ccggaatcgc tagtaatcgc ggatcagcat gccgcggtga atacgttccc | 1380 |
| gggtcttgta cacaccgccc gtcacaccac gagagttggt aacacccgaa gtcggtgagg | 1440 |

```
taaccttttg gagccagccg ccgaaggtgg gaccaatgat tggggtg          1487
```

<210> SEQ ID NO 4
<211> LENGTH: 1470
<212> TYPE: DNA
<213> ORGANISM: Bacillus fortis sp. IP-14

<400> SEQUENCE: 4

```
gacgaacgct ggcggcgtgc ctaatacatg caagtcgagc ggatgaagag gagcttgctc    60
cttggattca gcggcggacg ggtgagtaac acgtgggcaa cctgcctgta agactgggat   120
aactccggga aaccggggct aataccggat aacttctttt cccgcatggg gagaggttga   180
aagacggtta tgctgtcact tacagatggg cccgcggcgc attagctggt tggtggggta   240
acggcctacc aaggcgacga tgcgtagccg acctgagagg gtgatcggcc acactgggac   300
tgagacacgg cccagactcc tacgggaggc agcagtaggg aatcttccgc aatggacgaa   360
agtctgacgg agcaacgccg cgtgagtgac gaaggcttc gggtcgtaaa actctgttat   420
cagggaagaa caagtgtcgg ttaactgccg gtgccttgac ggtacctgac cagaaagcca   480
cggctaacta cgtgccagca gccgcggtaa tacgtaggtg gcaagcgttg tccggaatta   540
ttgggcgtaa agcgcgcgca ggcggcttct taagtctgat gtgaaagccc acggctcaac   600
cgtggagggt cattggaaac tgggaggctt gagtgcagaa gagaagagcg gaattccacg   660
tgtagcggtg aaatgcgtag agatgtggag gaacaccagt ggcgaaggcg gctctttggt   720
ctgtaactga cgctgaggcg cgaaagcgtg gggagcgaac aggattagat accctggtag   780
tccacgccgt aaacgatgag tgctaagtgt taggggtttt ccgcccctta gtgctgcagc   840
aaacgcatta agcactccgc ctggggagta cggccgcaag gctgaaactc aaaggaattg   900
acggggccc gcacaagcgg tggagcatgt ggtttaattc gaagcaacgc gaagaacctt   960
accaggtctt gacatcccgc tggccggcgc agagatgtgc cttccctttc ggggacagcg  1020
gtgacaggtg gtgcatggtt gtcgtcagct cgtgtcgtga gatgttgggt taagtcccgc  1080
aacgagcgca acccttgatc ttagttgcca gcattgagtt gggcactcta aggtgactgc  1140
cggtgacaaa ccggaggaag gtggggatga cgtcaaatca tcatgcccct tatgacctgg  1200
gctacacacg tgctacaatg gatggtacag agggcagcga accgcgagg tggagcgaat  1260
cccttaaaac cattctcagt tcggattgca ggctgcaact cgcctgcatg aagccggaat  1320
cgctagtaat cgcggatcag catgccgcgg tgaatacgtt cccgggcctt gtacacaccg  1380
cccgtcacac cacgagagtt tgtaacaccc gaagtcggtg aggtaaccgt aaggagccag  1440
ccgccgaagg tgggacagat gattgggtg                                    1470
```

<210> SEQ ID NO 5
<211> LENGTH: 1473
<212> TYPE: DNA
<213> ORGANISM: Lysinibacillus xylanilyticus sp. IP-23

<400> SEQUENCE: 5

```
gacgaacgct ggcggcgtgc ctaatacatg caagtcgagc gaacagatga ggagcttgct    60
cctctgatgt tagcggcgga cgggtgagta acacgtgggt aacctgccct gtagttgggg   120
ataacttcgg gaaaccgagg ctaataccga atgatacttg aaacacatg tttcgaagtt   180
gaaagatggt tctactatcg ctacaggatg gacccgcggc gcattagcta gttggtgagg   240
taacggctca ccaaggcgac gatgcgtagc cgacctgaga gggtgatcgg ccacactggg   300
```

-continued

```
actgagacac ggcccagact cctacgggag gcagcagtag ggaatcttcc acaatgggcg      360
aaagcctgat ggagcaacgc cgcgtgagtg aagaaggttt tcggatcgta aaactctgtt      420
gtaagggaag aacaagtaca gtagtaactg gctgtacctt gacggtacct tattagaaag      480
ccacggctaa ctacgtgcca gcagccgcgg taatacgtag gtggcaagcg ttgtccggaa      540
ttattgggcg taaagcgcgc gcaggcggtc ctttaagtct gatgtgaaag cccacggctc      600
aaccgtggag ggtcattgga aactggggga cttgagtgca aagaggaaa gtggaattcc      660
aagtgtagcg gtgaaatgcg tagagatttg aggaacacc agtggcgaag gcgactttct      720
ggtctgtaac tgacgctgag gcgcgaaagc gtggggagca acaggatta gatacctgg       780
tagtccacgc cgtaaacgat gagtgctaag tgttaggggg ttttccgcccc ttagtgctgc    840
agctaacgca ttaagcactc cgcctgggga gtacggtcgc aagactgaaa ctcaaaggaa    900
ttgacggggg cccgcacaag cggtggagca tgtggtttaa ttcgaagcaa cgcgaagaac    960
cttaccaggt cttgacatcc cgttgaccac tgtagagata tagtttcccc ttcggggggca  1020
acggtgacag gtggtgcatg gttgtcgtca gctcgtgtcg tgagatgttg ggttaagtcc   1080
cgcaacgagc gcaacccttg atcttagttg ccatcattta gttgggcact ctaaggtgac   1140
tgccggtgac aaaccggagg aaggtgggga tgacgtcaaa tcatcatgcc ccttatgacc   1200
tgggctacac acgtgctaca atggacgata caaacggttg ccaactcgcg agagggagct   1260
aatccgataa agtcgttctc agttcggatt gtaggctgca actcgcctac atgaagccgg   1320
aatcgctagt aatcgcggat cagcatgccg cggtgaatac gttcccgggc cttgtacaca   1380
ccgcccgtca caccacgaga gtttgtaaca cccgaagtcg tgaggtaac cttttggagc    1440
cagccgccga aggtgggata gatgattggg gtg                                1473
```

<210> SEQ ID NO 6
<211> LENGTH: 1477
<212> TYPE: DNA
<213> ORGANISM: Paenibacillus timonensis sp. IP-60

<400> SEQUENCE: 6

```
gacgaacgcc ggcggcgtgc ctaatacatg caagtcgagc ggacttgatg gagagcttgc     60
tctcctgatg gttagcggcg gacgggtgag taacacgtag gcaacctgcc tgcaagactg    120
ggataactac cggaaacggt agctaatacc ggatacgcag tttcctcgca tgagggagct    180
gggaaagacg gagcaatctg tcacttgcgg atgggcctgc ggcgcattag ctagttggtg    240
aggtaacggc tcaccaaggc gacgatgcgt aaccaacctg agagggtgaa cggccacact    300
gggactgaga cacggcccag actcctacgg gaggcagcag tagggaatct tccgcaatgg    360
acgaaagtct gacggagcaa cgccgcgtga gtgatgaagg ttttcggatc gtaaagctct    420
gttgccaggg aagaacgtcg ggtagagtaa ctgctgcccg agtgacggta cctgagaaga    480
aagcccggc taactacgtg ccagcagccg cggtaatacg taggggggcaa gcgttgtccg   540
gaattattgg gcgtaaagcg cgcgcaggcg gtcatgtaag tctggtgttt aatcccgggg    600
ctcaaccccg ggtcgcactg gaaactgggt gacttgagtg cagaagagga aagtggaatt    660
ccacgtgtag cggtgaaatg cgtagagatg tggaggaaca ccagtggcga aggcgacttt    720
ctgggctgta actgacgctg aggcgcgaaa gcgtggggag caaacaggat tagataccct    780
ggtagtccac gccgtaaacg atgaatgcta ggtgttaggg gtttcgatac ccttggtgcc    840
gaagttaaca cattaagcat tccgcctggg gagtacggtc gcaagactga aactcaaagg    900
aattgacggg gacccgcaca agcagtggag tatgtggttt aattcgaagc aacgcgaaga    960
```

| | |
|---|---|
| accttaccag gtcttgacat cccctgacc ggtctagaga taggcctttc cttcgggaca | 1020 |
| ggggagacag gtggtgcatg gttgtcgtca gctcgtgtcg tgagatgttg ggttaagtcc | 1080 |
| cgcaacgagc gcaacccttg actttagttg ccagcaggta aggctgggca ctctagagtg | 1140 |
| actgccggtg acaaaccgga ggaaggtggg gatgacgtca atcatcatg cccttatga | 1200 |
| cctgggctac acacgtacta caatggccgg tacaacggga agcgaaggag cgatctggag | 1260 |
| cgaatcttta gaagccggtc tcagttcgga ttgcaggctg caactcgcct gcatgaagtc | 1320 |
| ggaattgcta gtaatcgcgg atcagcatgc cgcggtgaat acgttcccgg gtcttgtaca | 1380 |
| caccgcccgt cacaccacga gagtttacaa cacccgaagt cggtgggta acccgcaagg | 1440 |
| gagccagccg ccgaaggtgg ggtagacgat tggggtg | 1477 |

<210> SEQ ID NO 7
<211> LENGTH: 1478
<212> TYPE: DNA
<213> ORGANISM: Paenibacillus curdlanolyticus sp. IP-75

<400> SEQUENCE: 7

| | |
|---|---|
| gacgaacgct ggcggcgtgc ctaatacatg caagtcgagc ggacccgatg gagtgcttgc | 60 |
| actcctgaag gttggcggca ggacgggtga gtaacacgta ggcaacctgc ccataagatc | 120 |
| gggataacat tcggaaacgg atgctaatac cggatagttg gactcctcgc atgaggggac | 180 |
| ctggaaaggc ggagcaatct gccgcttatg gatgggcctg cggcgcatta gctagttggt | 240 |
| ggggtaacgg cctaccaagg cgacgatgcg tagccgacct gagagggtga tcggccacac | 300 |
| tgggactgag acacggccca gactcctacg ggaggcagca gtagggaatc ttccgcaatg | 360 |
| gacgcaagtc tgacggagca acgccgcgtg agtgaggaag ccttcgggt cgtaaagctc | 420 |
| tgttgccagg gaagaacggg tagggagta actgccctg ccatgacggt acctgagaag | 480 |
| aaagccccgg ctaactacgt gccagcagcc gcggtaatac gtaggggca agcgttgtcc | 540 |
| ggaattattg ggcgtaaagc gcgcgcaggc ggctttgtaa gtcttgtgtt taagttcggg | 600 |
| gcttaacccc gtatcgcatg ggaaactgca aggcttgagt gcagaagagg aaagtggaat | 660 |
| tccacgtgta gcggtgaaat gcgtagagat gtggaggaac accagtggcg aaggcgactt | 720 |
| tctgggctgt aactgacgct gaggcgcgaa agcgtgggga gcaaacagga ttagatacct | 780 |
| tggtagtcca cgccgtaaac gatgaatgct aggtgttagg ggtttcgata cccttggtgc | 840 |
| cgaagttaac acattaagca ttccgcctgg ggagtacggt cgcaagactg aaactcaaag | 900 |
| gaattgacgg gacccgcac aagcagtgga gtatgtggtt taattcgaag caacgcgaag | 960 |
| aaccttacca ggtcttgaca tcccctgac cgggacagag atgttcttc ccttcggggc | 1020 |
| aggggagaca gtggtgcat ggttgtcgtc agctcgtgtc gtgagatgtt gggttaagtc | 1080 |
| ccgcaacgag cgcaacccct tgatcttagtt gccagcactt cgggtgggca ctctaagatg | 1140 |
| actgccggtg acaaaccgga ggaaggtggg gatgacgtca atcatcatg cccttatga | 1200 |
| cctgggctac acacgtacta caatggccgg tacaagggc tgcgaaatcg cgagatggag | 1260 |
| ccaatcccat caaagccggt ctcagttcgg attgcaggct gcaactcgcc tgcatgaagt | 1320 |
| cggaattgct agtaatcgcg gatcagcatg ccgcggtgaa tacgttcccg gtcttgtac | 1380 |
| acaccgcccg tcacaccagg agagtttaca cacccgaag tcggtggggt aacccgcaag | 1440 |
| ggagccagcc gccgaaggtg gggtagatga ttggggtg | 1478 |

<210> SEQ ID NO 8

```
<211> LENGTH: 1482
<212> TYPE: DNA
<213> ORGANISM: Bacillus ruris sp. IP-95

<400> SEQUENCE: 8
tcaggacgaa cgctggcggc gtgcctaata catgcaagtc gagcgaatct aaagggagct      60
tgctcccgga agattagcgg cggacgggtg agtaacacgt gggcaaccta cctgtaagtc     120
tgggataact tcgggaaacc ggagctaata ccggataatt tctttcttcg catgaagaaa     180
ggttgaaaga cggctttgct gtcacttaca gatgggcccg cggcgcatta gttagttggt     240
gaggtaacgg ctcaccaaga ccacgatgcg tagccgacct gagagggtga tcggccacac     300
tgggactgag acacggccca gactcctacg ggaggcagca gtagggaatc ttccgcaatg     360
gacgaaagtc tgacggagca acgccgcgtg agtgaagaag gtcttcggat cgtaaaactc     420
tgttatcagg gaagaacaag taccggagtc actgccggta ccttgacggt acctgaccag     480
aaagccacgg ctaactacgt gccagcagcc gcggtaatac gtaggtggca agcgttgtcc     540
ggaattattg ggcgtaaagc gcgcgcaggc ggttctttaa gtctgatgtg aaatcttgcg     600
gctcaaccgt gagcggtcat tggaaactgg agaacttgag tgcagaagag aagagcggaa     660
ttccacgtgt agcggtgaaa tgcgtagaga tgtggaggaa caccagtggc gaaggcggct     720
ctttggtctg taactgacgc tgaggcgcga aagcgtgggg agcgaacagg attagatacc     780
ctggtagtcc acgccgtaaa cgatgagtgc taagtgttag agggtttccg ccctttagtg     840
ctgcagcaaa cgcattaagc actccgcctg gggagtacgg ccgcaaggct gaaactcaaa     900
ggaattgacg gggcccgca caagcggtgg agcatgtggt ttaattcgaa gcaacgcgaa     960
gaaccttacc aggtcttgac atcctttgac aaccctagag atagggcgtt cccttcggg    1020
ggacaaagtg acaggtggtg catggttgtc gtcagctcgt gtcgtgagat gttgggttaa    1080
gtcccgcaac gagcgcaacc cttgaaatta gttgccagca ttcagttggg cactctaatt    1140
tgactgccgg tgacaaaccg gaggaaggtg gggatgacgt caaatcatca tgccccttat    1200
gacctgggct acacacgtgc tacaatggat ggtacagagg gctgcaagac cgcgaggttt    1260
agccaatccc ttaaaaccat tctcagttcg gattgtaggc tgcaactcgc ctacatgaag    1320
ccggaatcgc tagtaatcgc ggatcagcat gccgcggtga atacgttccc gggccttgta    1380
cacaccgccc gtcacaccac gagagtttgt aacacccgaa gtcggtgagg taaccttttg    1440
gagccagccg ccgaaggtgg gacagatgat tggggtgaag tc                       1482

<210> SEQ ID NO 9
<211> LENGTH: 1506
<212> TYPE: DNA
<213> ORGANISM: Bacillus thermoamylovorans sp. N-11 (NITE BP-863)

<400> SEQUENCE: 9
gacgaacgct ggcggcgtgc ctaatacatg caagtcgagc gaaccaataa gaagcttgct      60
ttttgttggt tagcggcgga cggtgagta acacgtggga aacctgcctg taagaccggg     120
ataactccgg gaaaccggtg ctaataccgg atagattatc tttccgcctg gagagataag     180
gaaagatggc twttgccatc acttacagat gggcccgcgg cgcattagct agttggtgag     240
gtaacggctc accaaggcga cgatgcgtag ccgacctgag agggtgatcg ccacactgg     300
gactgagaca cggcccagac tcctacggga ggcagcagta gggaatcttc gcaatggac     360
gaaagtctga cggagcaacg ccgcgtgagc gaagaaggtc ttcggatcgt aaagctctgt     420
tgttagggaa gaacaagtat cggaggaaat gccggtacct tgacggtacc tgacgagaaa     480
```

```
gccacggcta actacgtgcc agcagccgcg gtaatacgta ggtggcaagc gttgtccgga      540
wttattgggc gtaaagcgcg cgcaggcggt cctttaagtc tgatgtgaaa tcttgcggct      600
caaccgcaag cggtcattgg aaactggggg acttgagtgc agaagaggaa agcggaattc      660
cacgtgtagc ggtgaaatgc gtagagatgt ggaggaacac cagtggcgaa ggcggctttc      720
tggtctgtaa ctgacgctga ggcgcgaaag cgtgggagc aaacaggatt agataccctg       780
gtagtccacg ccgtaaacga tgagtgctaa gtgttgagg gtttccgccc ttcagtgctg       840
cagctaacgc attaagcact ccgcctgggg agtacggtcg caagactgaa actcaaagga      900
attgacgggg gcccgcacaa gcggtggagc atgtggttta attcgaagca acgcgaagaa      960
ccttaccagg tcttgacatc tcctgaccgc cctggagaca gggtcttccc ttcggggaca     1020
ggatgacagg tggtgcatgg ttgtcgtcag ctcgtgtcgt gagatgttgg gttaagtccc     1080
gcaacgagcg caacccttgg ttctagttgc cagcattcag ttgggcactc tagagcgact     1140
gccggcgaca gtcggagga aggtggggat gacgtcaaat catcatgccc cttatgacct      1200
gggctacaca cgtgctacaa tggatggtac aaagggcagc gaagcggcga cgcatragcg     1260
aatcccagaa aaccattctc agttcggatt gcaggctgca actcgcctgc atgaagccgg     1320
aatcgctagt aatcgcggat cagcatgccg cggtgaatac gttcccgggc cttgtacaca     1380
ccgcccgtca caccacgaga gtttgtaaca cccgaagtcg gtgaggtaac cgcaaggagc     1440
cagccgccga aggtgggaca gatgattggg gtgaagtcgt aacaaggtag ccgtatcgga     1500
aggtgc                                                                1506

<210> SEQ ID NO 10
<211> LENGTH: 1509
<212> TYPE: DNA
<213> ORGANISM: Bacillus coagulans sp. N-16

<400> SEQUENCE: 10
gacgaacgct ggcggcgtgc ctaatacatg caagtcgtgc ggaccttta aaagcttgct        60
tttaaaaggt tagcggcgga cgggtgagta acacgtgggc aacctgcctg taagatcggg      120
ataacgccgg gaaaccgggg ctaataccgg atagtttttt cctccgcatg gaggaaaaag      180
gaaagacggc ttcggctgtc acttacagat gggcccgcgg cgcattagct agttggtggg      240
gtaacggctc accaaggcaa cgatgcgtag ccgacctgag agggtgatcg ccacattgg       300
gactgagaca cggcccaaac tcctacggga ggcagcagta gggaatcttc cgcaatggac      360
gaaagtctga cggagcaacg ccgcgtgagt gaagaaggcc ttcgggtcgt aaaactctgt      420
tgccggggaa gaacaagtgc cgttcgaaca gggcggcgcc ttgacggtac ccggccagaa      480
agccacggct aactacgtgc cagcagccgc ggtaatacgt aggtggcaag cgttgtccgg      540
aattattggg cgtaaagcgc gcgcaggcgg cttcttaagt ctgatgtgaa atcttgcggc      600
tcaaccgcaa gcggtcattg aaactgggag gcttgagtg cagaagagga gagtggaatt      660
ccacgtgtag cggtgaaatg cgtagagatg tggaggaaca ccagtggcga aggcggctct      720
ctggtctgta actgacgctg aggcgcgaaa gcgtggggag caaacaggat tagataccct      780
ggtagtccac gccgtaaacg atgagtgcta agtgttgagg ggtttccgcc ctttagtgct      840
gcagctaacg cattaagcac tccgcctggg gagtacggcc gcaaggctga aactcaaagg      900
aattgacggg ggcccgcaca gcggtggagc atgtggttt aattcgaagc aacgcgaaga      960
accttaccag gtcttgacat cctctgacct ccctggagac agggccttcc ccttcggggg     1020
```

-continued

```
acagagtgac aggtggtgca tggttgtcgt cagctcgtgt cgtgagatgt tgggttaagt    1080
cccgcaacga gcgcaaccct tgaccttagt tgccagcatt cagttgggca ctctaaggtg    1140
actgccggtg acaaaccgga ggaaggtggg gatgacgtca aatcatcatg ccccttatga    1200
cctgggctac acacgtgcta caatggatgg tacaaagggc tgcgagaccg cgaggttaag    1260
ccaatcccag aaaaccattc ccagttcgga ttgcaggctg caacccgcct gcatgaagcc    1320
ggaatcgcta gtaatcgcgg atcagcatgc cgcggtgaat acgttcccgg gccttgtaca    1380
caccgcccgt cacaccacga gagtttgtaa cacccgaagt cggtgaggta acctttacgg    1440
agccagccgc cgaaggtggg acagatgatt ggggtgaagt cgtaacaagg tagccgtatc    1500
ggaaggtgc                                                            1509
```